US011221440B2

(12) United States Patent
Lebhar et al.

(10) Patent No.: US 11,221,440 B2
(45) Date of Patent: Jan. 11, 2022

(54) SYSTEMS AND METHODS FOR ILLUMINATION OF MEDICAL TUBING

(71) Applicant: DUKE UNIVERSITY, Durham, NC (US)

(72) Inventors: Michael Lebhar, Durham, NC (US); Konstantinos Economopoulos, Durham, NC (US); Anshu Jonnalagadda, Durham, NC (US); Shikha Sharma, Durham, NC (US); Kevin Tian, Durham, NC (US); Jacqueline Vaughn, Durham, NC (US); Paul Fearis, Durham, NC (US); Eric Richardson, Durham, NC (US)

(73) Assignee: Duke University, Durham, NC (US)

(*) Notice: Subject to any disclaimer, the term of this patent is extended or adjusted under 35 U.S.C. 154(b) by 0 days.

(21) Appl. No.: 17/225,679

(22) Filed: Apr. 8, 2021

(65) Prior Publication Data
US 2021/0318479 A1 Oct. 14, 2021

Related U.S. Application Data

(60) Provisional application No. 63/007,007, filed on Apr. 8, 2020.

(51) Int. Cl.
*F21V 8/00* (2006.01)
*F21V 23/00* (2015.01)
*F21V 21/088* (2006.01)
*A61M 39/08* (2006.01)
*F21V 23/04* (2006.01)
*F21Y 115/10* (2016.01)

(52) U.S. Cl.
CPC ............. *G02B 6/001* (2013.01); *A61M 39/08* (2013.01); *F21V 21/088* (2013.01); *F21V 23/003* (2013.01); *F21V 23/04* (2013.01); *G02B 6/0006* (2013.01); *A61M 2205/587* (2013.01); *F21Y 2115/10* (2016.08)

(58) Field of Classification Search
CPC ...... G02B 6/001; A61M 39/08; F21V 21/088; F21V 23/003; F21V 23/04
See application file for complete search history.

(56) References Cited

U.S. PATENT DOCUMENTS

| | | | |
|---|---|---|---|
| 6,393,192 B1 * | 5/2002 | Koren ................. | G02B 6/0006 239/12 |
| 9,308,051 B2 * | 4/2016 | Adams ............. | A61M 25/0043 |
| 10,064,991 B2 * | 9/2018 | Provost .................. | G06F 21/35 |
| 10,232,107 B2 * | 3/2019 | Utz ..................... | F21V 33/0068 |

(Continued)

*Primary Examiner* — Bryon T Gyllstrom
(74) *Attorney, Agent, or Firm* — Quarles & Brady LLC

(57) ABSTRACT

A system for illuminating medical tubes is disclosed. The system includes an optical fiber secured to and extending along a length of a medical tube, and a light source configured to transmit a light through the optical fiber. The system further includes a controller in communication with the light source, and configured to control the light source. Additionally, the system includes an optical junction having a first input configured to secure a portion of medical tubing, a second input configured to receive and direct the light from the light source to the optical fiber, and an output configured to secure the optical fiber and the medical tube. The first input and the output are fluidly connected via the optical junction. The light illuminates the medical tubing via the optical fiber.

23 Claims, 15 Drawing Sheets

(56) References Cited

U.S. PATENT DOCUMENTS

| | | | | |
|---|---|---|---|---|
| 2004/0105278 A1* | 6/2004 | Currie | ................... | G02B 6/001 362/551 |
| 2013/0123743 A1* | 5/2013 | Adams | ................ | F21V 33/0068 604/500 |
| 2013/0208497 A1* | 8/2013 | Provost | ............... | F21V 33/0068 362/555 |

* cited by examiner

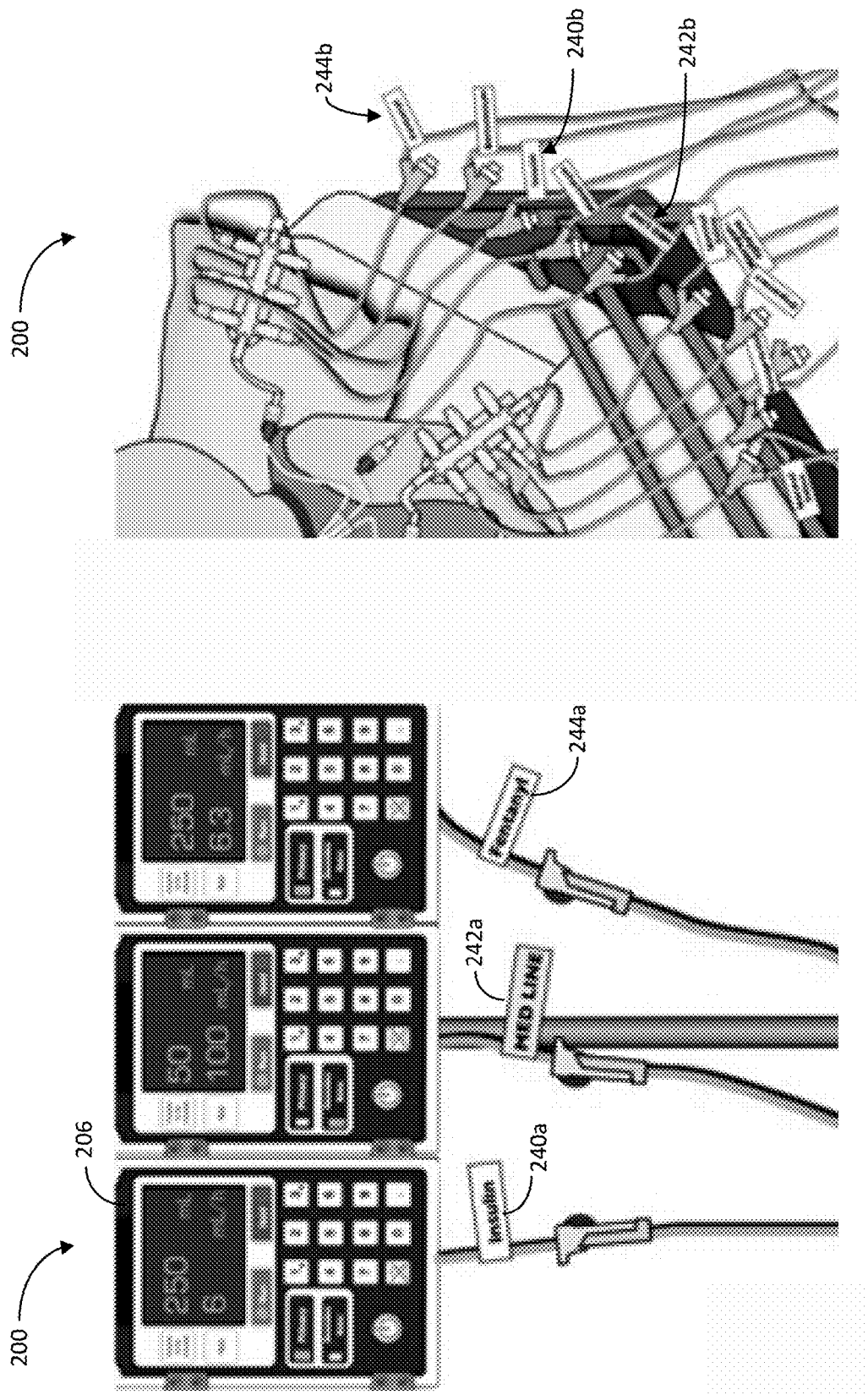

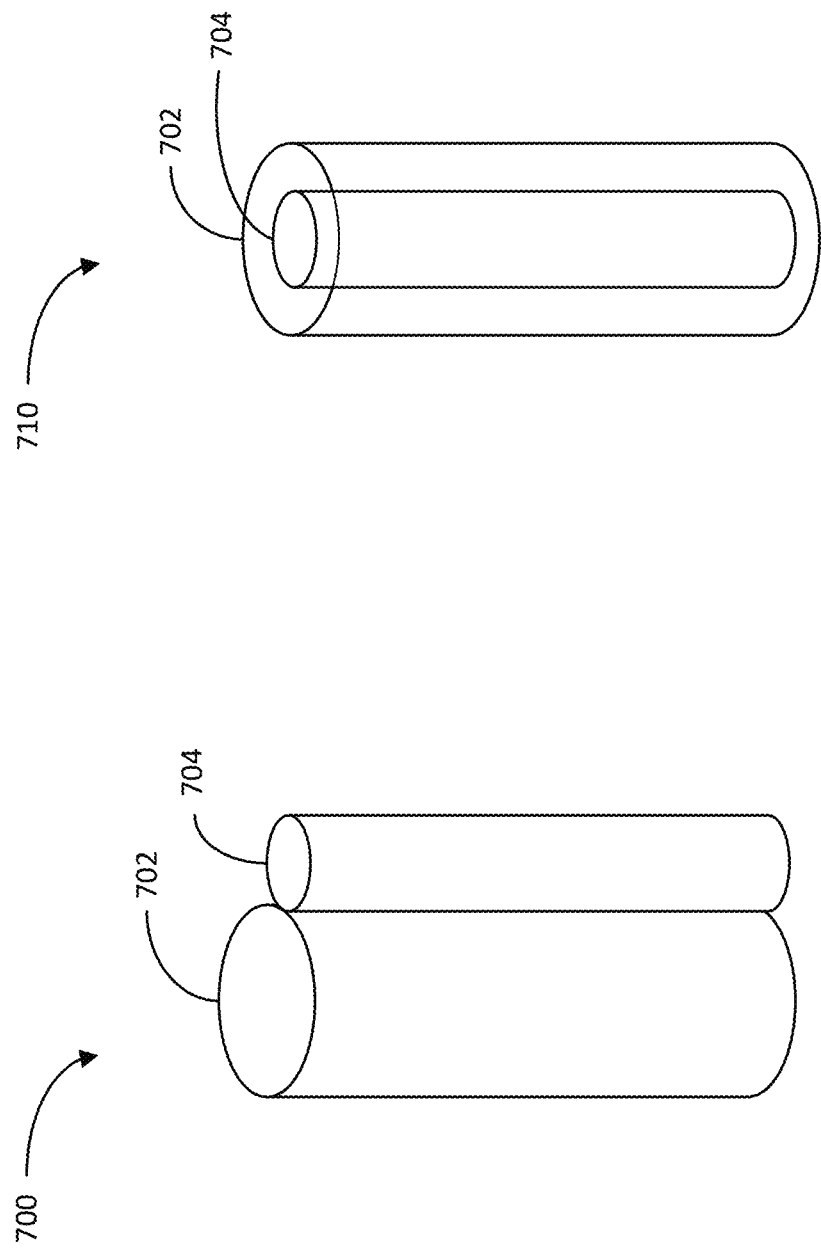

SYSTEMS AND METHODS FOR ILLUMINATION OF MEDICAL TUBING

CROSS-REFERENCES TO RELATED APPLICATIONS

The present application claims priority to U.S. Provisional Patent Application No. 63/007,007, filed Apr. 8, 2020, entitled "Illumination of Medical Tubing," which is hereby incorporated by reference in its entirety.

STATEMENT REGARDING FEDERALLY SPONSORED RESEARCH

Not Applicable.

BACKGROUND OF THE INVENTION

In some clinical care scenarios, patients may require a number of medical tubes, such as intravenous (IV) lines, electrocardiography wires, extracorporeal membrane oxygenation infusion catheters, pulse oximeter tubing, endotracheal tubes. As the number of IV lines increases, so does the opportunity for error in accessing the lines, such as when inserting or removing, adding medication via syringes, and replacing or changing supply medication. Additionally, extra time is needed for medical personnel to accurately trace lines between the patient and the supply source (e.g., a hanging IV bag). This can be undesirable from a staffing perspective, as well as disastrous in times of critical care. Hence, there is an ongoing and unmet need for systems and methods enabling safe, efficient, and reliable interactions with medical tubing.

SUMMARY OF THE INVENTION

The present disclosure includes a system for illuminating medical tubes. The system includes an optical fiber secured to and extending along a length of a medical tube, and a light source configured to transmit a light through the optical fiber. The system further includes a controller in communication with the light source, and configured to control the light source. Additionally, the system includes an optical junction having a first input configured to secure a portion of medical tubing, a second input configured to receive and direct the light from the light source to the optical fiber, and an output configured to secure the optical fiber and the medical tube. The first input and the output are fluidly connected via the optical junction. Further, the light illuminates the medical tubing via the optical fiber.

In some embodiments, the optical fiber is secured to the medical tube via co-extrusion. Additionally, in some embodiments, the controller is configured to activate the light source in response to a user input. The controller can be configured to deactivate the light source after a predefined illumination time. Additionally, the controller can be configured to pulse the light source at a fixed or variable frequency. In some embodiments, the optical fiber is secured to the medical tube via a plurality of clamps disposed along the length of the medical tube. The plurality of clamps can be configured to slide along the medical tube.

In some embodiments, the system can include a multi-channel adapter in communication with the light source and controller, with the multi-channel adapter connected to a plurality of optical junctions. In some embodiments, the controller is configured to receive a user input, determine which channel of the multi-channel adapter is associated with the user input, and activate the light source for the determined channel. In some embodiments, each of the plurality of optical junctions corresponds to one of a plurality of optical fibers. In some embodiments, the controller is configured to receive the user input from at least one of a push button, a touch-screen, a keyboard, a wired user device, or a wireless user device. In some embodiments, the illumination of the optical fiber is continuous along the length of the medical tube.

The present disclosure further includes a method for illuminating medical tubing. The method includes coupling a first end of medical tubing to a first input of an optical junction, and guiding light from a light source to a second input of the optical junction. The method further includes securing an optical fiber to the medical tubing at an output of the optical junction, causing the first input to be fluidly connected to the output of the optical junction and the second input to be connected to the output of the optical junction. Additionally, the method includes, in response to a user input, activating the light source to provide the light.

In some embodiments, the optical fiber and the medical tubing are co-extruded or otherwise manufactured as an integrated component. The method can further include deactivating the light source after a predefined amount of time. Additionally, the method can include pulsing the light source at a fixed frequency for the predefined amount of time. In some embodiments, the method includes, prior to activating the light source: determining a channel corresponding to a multi-channel adapter, based on the user input; and providing the light to the optical junction by activating the channel. In some embodiments, the method includes coupling a second end of the medical tubing to a drip chamber of an IV bag.

The present disclosure further includes a system for illuminating medical tubing within a multi-infusion system. The system includes a plurality of illuminating tubes, each illuminating tube including a medical tube secured to an optical fiber. The system further includes a light source configured to transmit a light through the optical fiber, and a plurality of optical junctions. Each optical junction includes a first input configured to secure a portion of medical tubing, a second input configured to receive and direct the light to the optical fiber such that the optical fiber illuminates, and an output configured to secure one illuminating tube of the plurality of illuminating tubes. The first input and the output are fluidly connected via the optical junction. The system further includes a multi-channel adapter in communication with the light source and each of the plurality of optical junctions, where the multi-channel adapter is configured to selectively provide the light to any one of the plurality of optical junctions.

In some embodiments, the multi-channel adapter selectively provides the light to a desired optical junction in response to a user input. In some embodiments, the multi-channel adapter is configured to provide the light to only one optical junction at any particular time. The system can include a controller in communication with the light source and the multi-channel adapter. The controller can be configured to receive a user input; determine, from the user input, a corresponding optical junction from the plurality of optical junctions; retrieve, from a controller memory, information associated with an infusion bag, where the infusion bag is fluidly connected to the first input of the corresponding optical junction; and output the information associated with the infusion bag to at least one of a user device or a display. In some embodiments, the light source is a laser or at least one light-emitting diode.

BRIEF DESCRIPTION OF THE DRAWINGS

FIG. 2C is a pictorial diagram of a conventional line identification method corresponding to the multi-infusion system of FIG. 2A.

FIG. 2D is a pictorial diagram of a conventional line identification method corresponding to the multi-infusion system of FIG. 2A.

FIG. 12 is a diagram of illuminated tubing, in accordance with embodiments of the present disclosure.

FIG. 13 is a diagram of another illuminated tubing, in accordance with embodiments of the present disclosure.

Like reference numerals will be used to refer to like parts from Figure to Figure in the following description of the drawings.

DETAILED DESCRIPTION OF THE INVENTION

Figure 1:
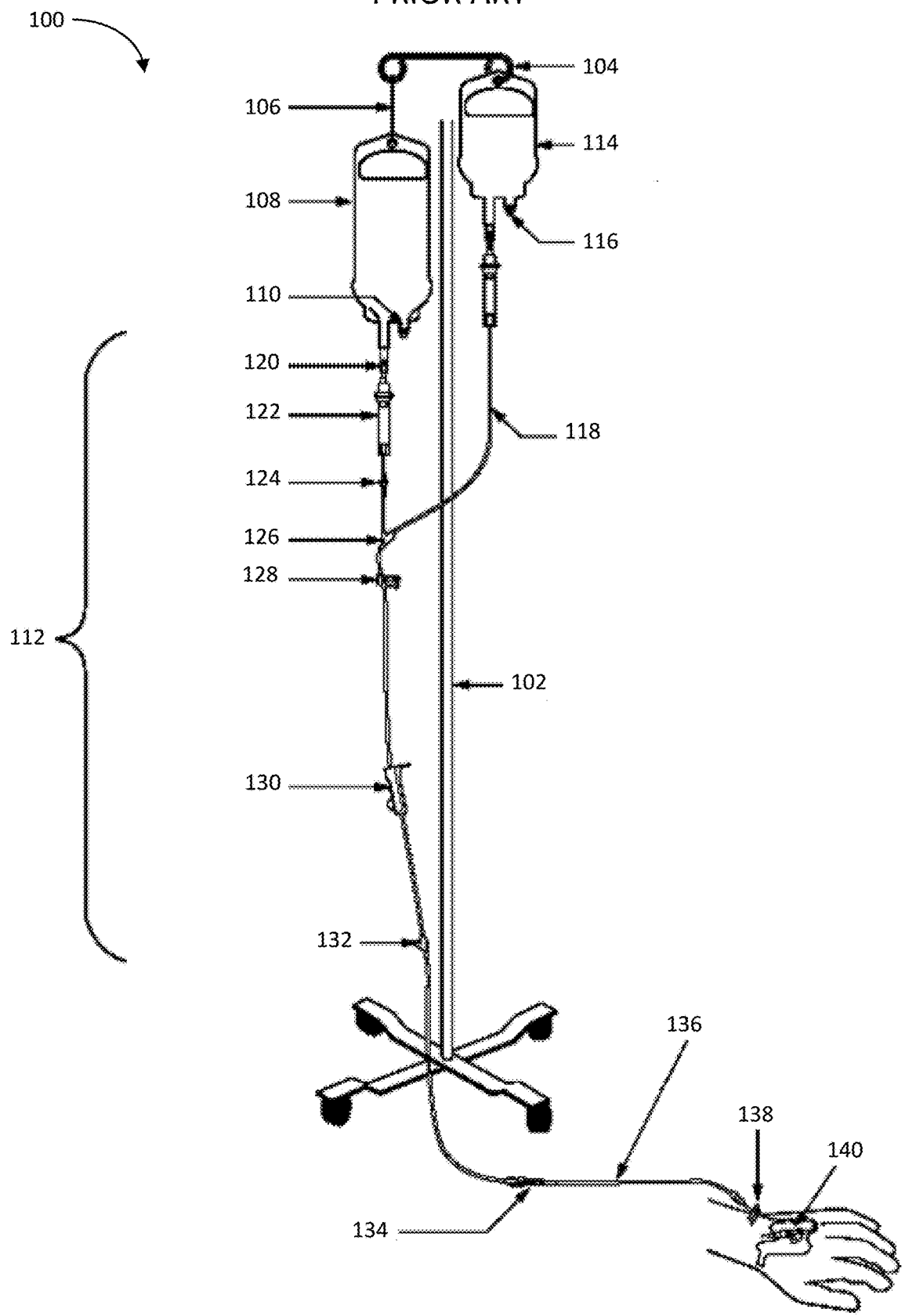
FIG. 1 is a diagram of a prior art intravenous (IV) system.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention. While the concepts of the disclosure are described in relation to intravenous tubing, it should be understood that it is equally applicable to other clinical scenarios involving medical tubing, and where identification among multiple lines is otherwise desirable. Additionally, the concepts of the present disclosure may provide similar beneficial implications in other industry settings, such as tracing wires in control panels, cables of electronic devices, pipes in construction buildings, etc. Accordingly, the present disclosure can include systems and methods for illuminating tubes, wires, and cables, among other things.

Acutely ill patients with life-threatening conditions require constant care, monitoring, and a number of life-sustaining medications. Tight control of medication dosing and the need for immediate therapeutic effects make the controlled administration of medication directly into a patient's bloodstream an invaluable tool for patient care. The administration of medication and fluids into a patient's veins is referred to as intravenous (IV) administration, and about 90% of hospitalized patients receive medications this way.

Referring to FIG. 1, a conventional IV system 100 is shown. The conventional IV system ("system") 100 is shown to include an IV pole 102, and a hook 104 extending from the IV pole 102. In some configurations, the system 100 can include an extender 106, which can be attached to one of the hooks (e.g., hook 104). As shown, the extender 106 supports the hanging of a primary IV bag 108. The primary IV bag 108 includes an injection port 110. The primary IV bag 108 is connected to a primary IV tubing 112. The system 100 can further include a secondary IV bag 114, which can hang directly or indirectly (e.g., via an extender) from a hook. The secondary IV bag 114 includes an injection port 116. The secondary IV bag 114 is connected to a secondary IV tubing 118.

In some configurations, the primary IV tubing 112 can include a sterile spike 120 connected to the primary IV bag 108 and a drip chamber 122 located beneath the sterile spike 120. The primary IV tubing 112 is further shown to include a back check valve 124, and a port 126. The port 126 is connected to the secondary IV tubing 118. In some configurations, a slider clamp 128 and/or a roller clamp 130 can be positioned along the primary IV tubing 112. A port 132 may also be provided further down the primary IV tubing 112.

The system 100 can further include a luer lock 134, which can connect the primary IV tubing 112 with extension tubing 136. A clamp 138 can be provided proximate to a cannula 140, and the cannula 140 is inserted in the patient. The system 100 is configured to provide a fluid to a patient, from the primary IV bag 108 and the secondary IV bag 114 via the primary IV tubing 112 and the secondary IV tubing 118.

In some clinical settings, infusion pumps may be used for IV administration. Infusion pumps accurately control the amount of medication patients receive and the rate at which the medication is administered. Still, medication errors associated with infusion therapy are well-documented.

Intensive care units (ICUs) contain critically ill patients, who often require a high number of infusions (in particular, high-alert continuous IV medications). To add further complexity, ICU patients are often medically unstable, requiring immediate and unplanned interventions by nurses and doctors. ICUs (similarly to general care units) experience IV administration errors. However, within the ICU, these errors are associated with greater severity, length of stay, and cost.

Setting up more than one primary continuous IV infusion is a common task when caring for acutely ill patients, and may be required when: multiple new IV infusions are prescribed to be initiated immediately (e.g., a new patient is admitted who requires multiple IV therapies); patients are transferred to a new clinical unit and infusions have to be set up again because of differences in infusion equipment (e.g., pump manufacturer/model, drug libraries), medication concentrations, or decentralized inventory management (requiring that pumps be returned to their home unit); or all IV containers, tubing, and connectors must be changed as part of a "line change" (a best practice to reduce the risk of infection).

Infusion setup risks may be compounded with multiple IV infusions. The number of infusions at a patient's bedside increases both the physical complexity (e.g., more IV containers, pumps, IV tubing, poles), as well as the cognitive load (e.g., managing multiple drug orders). Medication errors are more common in clinical environments where patients are receiving multiple medications. Research has indicated that each additional IV drug administration increases the likelihood of adverse drug events by 3%.

Once an IV infusion has been set up, clinicians must be able to quickly and accurately identify its contents (e.g., medication, concentration), status (e.g., infusing, stopped/paused), and pathway (e.g., the access port to which the infusion is connected, other connected infusions).

Ideally, each infusion should have a visually distinct and discrete pathway, beginning at the IV container and ending at the patient. Instead, however, IV components (particularly IV tubes in multi-infusion environments) frequently become twisted and easily confused. The resulting visual clutter, commonly referred to as "spaghetti syndrome," makes it challenging for even experienced nurses to quickly and accurately identify infusions and their components. "Spaghetti syndrome" can create frustration and tension between staff (e.g., between transferring units, at shift handovers), but it can also result in patient harm, particularly in critically ill patients, who often require urgent and frequent changes in therapy.

First, patient harm may arise because of delays in critical changes to treatment while a nurse sorts through a complex setup. Sorting through the setup can require significant nursing resources (including time). Second, spaghetti syndrome may also make it difficult for nurses to correctly identify infusion components, which can result in patient harm. Infusion confusion is known to contribute to the incorrect identification of lines (e.g., during manual line tracing).

Referring now to FIGS. 2A-2D, an example of a multi-infusion environment is shown via an IV system 200. As shown, twelve distinct fluids are connected variously to the patient. As an example, IV bag 202 is connected to IV tubing 204, which is in communication with an infusion pump 206. Near the patient, multiple IV lines terminate at a multiport connector 208. The multiport connector 208 is further connected to an access port 210 (a connection point to an IV catheter that provides a unique and independent pathway to the patient's bloodstream). An example of "spaghetti syndrome" is provided by reference box 212 in FIG. 2A. As shown, the large number of IV lines and devices are difficult to distinguish due to the jumbled appearance.

Figure 2A:
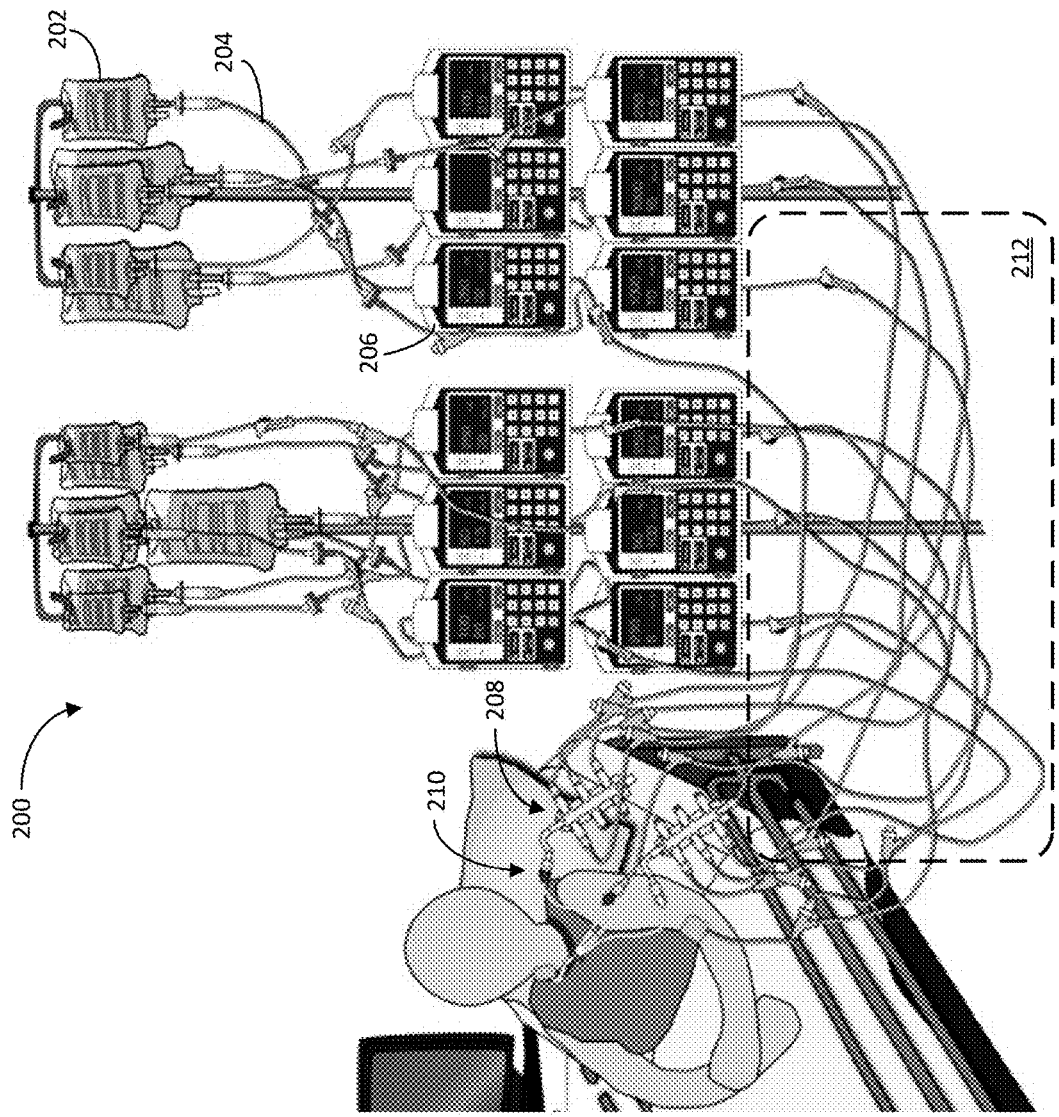
FIG. 2A is a pictorial diagram of a prior art multi-infusion system.
Figure 2B:
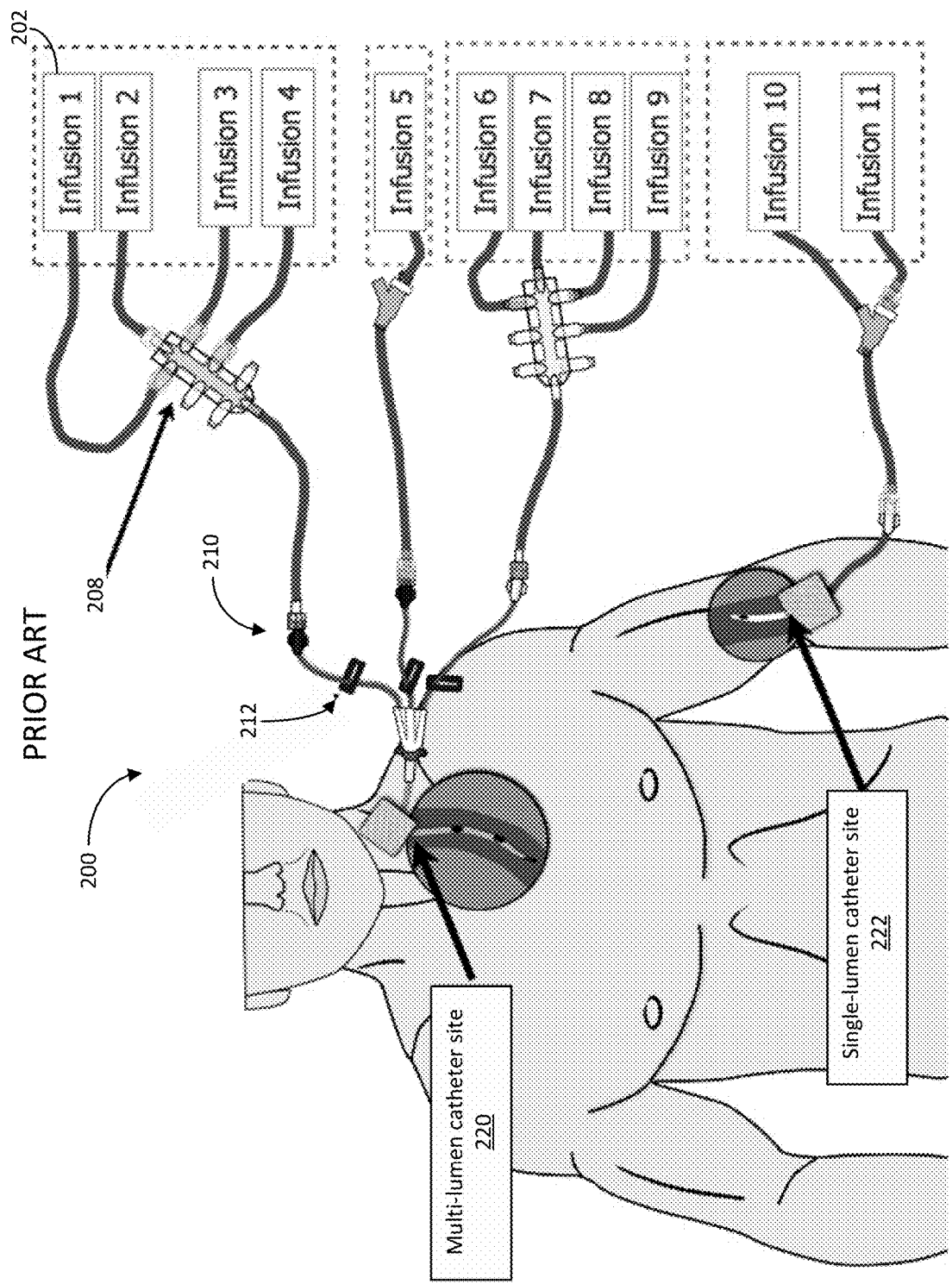
FIG. 2B is a pictorial diagram of a patient-side of the multi-infusion system of FIG. 2A.

FIG. 2B illustrates the IV system 200 at the patent-side connections. Notably, without any identifying features at the patient, it becomes impossible to quickly and accurately determine which IV lines correspond to which IV bags. As shown, the multiport connector 208 and the access port 210 correspond to one branch connected to the patient via a multi-lumen catheter site 220. The multiport connector 208 is shown in connection with four IV bags (infusions 1-4). In contrast, a single-lumen catheter site 222 is shown in connection with two IV bags (infusions 10-11).

To complete various tasks (e.g., disconnect an infusion, administer a manual IV push), nurses must routinely identify and verify an infusion pathway by physically sliding their hands along the tubing from the IV container to the patient access port (or vice versa). This is referred to as "line tracing," and can include physical tracing around various obstructions (e.g., patient gowns, other tubing, pumps).

Nursing best practices include tracing lines from the patient to the point of origin (or vice versa) in the following situations: 1) before making any connections/disconnections (e.g., connecting a secondary IV infusion to a primary IV infusion, administering a manual IV push) or altering IV infusions (e.g., increasing the flow rate); 2) during staff hand-off processes (e.g., patient's arrival to a new unit, staff shift changes); and 3) several times a shift when double-checking all IV solutions. The process of line tracing can be very time and resource intensive, and can lead to errors (e.g, choosing the wrong IV tubing to trace, inadvertently switching to the wrong IV tubing during tracing). Ultimately, incorrect line tracing can result in a patient receiving an unintended medication or dosage, failing to receive a desired medication or dosage, or receiving a mixture of incompatible medications due to misidentification.

Labeling infusions is a well-recognized strategy for informing clinicians about infusion setups, placing information where it is needed and reducing memory load. However, there is not a "standardized" labeling practice between hospitals, or even among clinical units and clinicians.

The use of adhesive labels (including preprinted labels) is a common method for labeling. Alternatively, it is also common for nurses (particularly those in critical care) to use handwritten adhesive labels, which can indicate the drug name and access port, among other things.

Referring to FIGS. 2C and 2D, an example method of labeling is shown via the system 200. As shown, an ID tag 240a identifying "insulin" is attached to the IV line proximate to the infusion pump 206. A corresponding ID tag 240b which also identifies "insulin" is attached to the IV line proximate to the injection port proximate to the patient. As shown, another ID tag 242a identifying "MED LINE" is attached to the IV line proximate to the infusion pump. A corresponding ID tag 242b which also identifies "MED LINE" is attached to the IV line proximate to the injection port proximate to the patient. Notably, the MED LINE ID tags 242a, 242b are brightly colored relative to the other ID tags. In some scenarios, it can be beneficial to efficiently identify the emergency medical line. As shown, another ID tag 244a identifying "fentanyl" is attached to the IV line proximate to the infusion pump. A corresponding ID tag 244b which also identifies "fentanyl" is attached to the IV line proximate to the injection port proximate to the patient.

Notably, implementing any type of adhesive labels requires time and compliance, and can introduce new errors. Such ad hoc identification/labeling systems can lead to many issues, such as: placement of a label on an incorrect component, confusing or illegible labels, insufficient adherence to the desired component, reduced label visibility based on the viewing angle (e.g., wrapped around IV tubing), emergency medical line(s) being visually indistinguishable from other infusions, cleaning and infection-control challenges, and the display of outdated information (e.g., pump labels not removed when a medication is discontinued, and the pump is subsequently reused for a new and different infusion). Referring to FIGS. 2C and 2D, for example, mixing up ID tags 240*a* and 244*a* (thus misidentifying fentanyl as insulin), could be a fatal error.

Notably, the use of labels fails to provide information about an infusion along the pathway. At best, information about the infusion is only partially communicated along the infusion pathway (e.g., at the IV container label, infusion pump display). In particular, there is a lack of information about infusion contents below the pump (e.g., at the patient's bedside).

Color-tinted IV tubing has been suggested (and commercially marketed) as a way to help minimize infusion identification errors. Color-tinted tubing is believed to assist clinicians in distinguishing between infusions and visually tracing infusion pathways. However, the U.S. Institute for Safe Medication Practices (ISMP) has identified several concerns and risks related to color-tinted tubing, which have led to harmful consequences in practice.

Color-tinted tubing can result in color mix-ups. As an example, color-tinted tubing may be mixed up with other colors used in health care (e.g., yellow-tinted tubing may be confused with yellow-striped epidural tubing), or the tubing color may be altered by the infusate color (e.g., a red drug may give blue tubing a purple tint). Further, color-tinted IV lines may not match existing color-coded labels, leading to confusion.

Color-tinted tubing can appear different to different people (e.g., some staff may have color-blindness. Poor lighting may also contribute to the misperception of color. Additionally, humans have poor color memory, particularly for similar shades, limiting the scope of a color-coding scheme.

In addition to the above, there is no established or universal medication color scheme in health care. Colors used between clinical units, hospitals, or vendors are often different and can have very different meanings. In practice, colored IV tubing can lead users to rely solely on color to identify an infusion (i.e., instead of line tracing to confirm infusion contents and connections).

The use of wireless lighting has also been suggested (and commercially marketed) as a way to help minimize infusion identification errors. In particular, several wireless lighting components can be removably attached to portions of an existing IV line (e.g., a first light near the IV bag, a second light near the infusion pump, and a third light near the patient access point). However, the use of such wireless lighting components fails to address many of the issues associated with the conventional adhesive labels.

Similarly to the attachment of labels, attaching multiple wireless lighting components along each IV line can introduce user error (e.g., incorrectly attaching one or more of the lights to a different, unintended IV line). Tangled IV lines can cause accidental detachment of the light from the proper IV line. Notably, the use of wireless lighting components fails to provide information about an infusion, in a continuous method, along the pathway. At best, information about the infusion is only partially communicated along the infusion pathway (e.g., at the location of each light).

Due to the issues outlined above, research shows that nurses still default to manually tracing the IV lines, just as with the adhesive labels. Ironically, the addition of attached lighting increases the complexity of line tracing, as nurses must physically trace around these additional line obstructions (which can increase the tracing time and introduce error).

Accordingly, the present disclosure is directed to the ongoing and unmet need for systems and methods enabling safe, efficient, and reliable interactions with medical tubing. Specifically, the present disclosure includes systems and methods for the illumination of medical tubing.

As used herein, the term "light source" can include various systems and methods for generating and/or directing light. Some non-limiting examples of light sources include: light-emitting diodes (LEDs), electroluminescent (EL) wires or components, and lasers.

Figure 3:
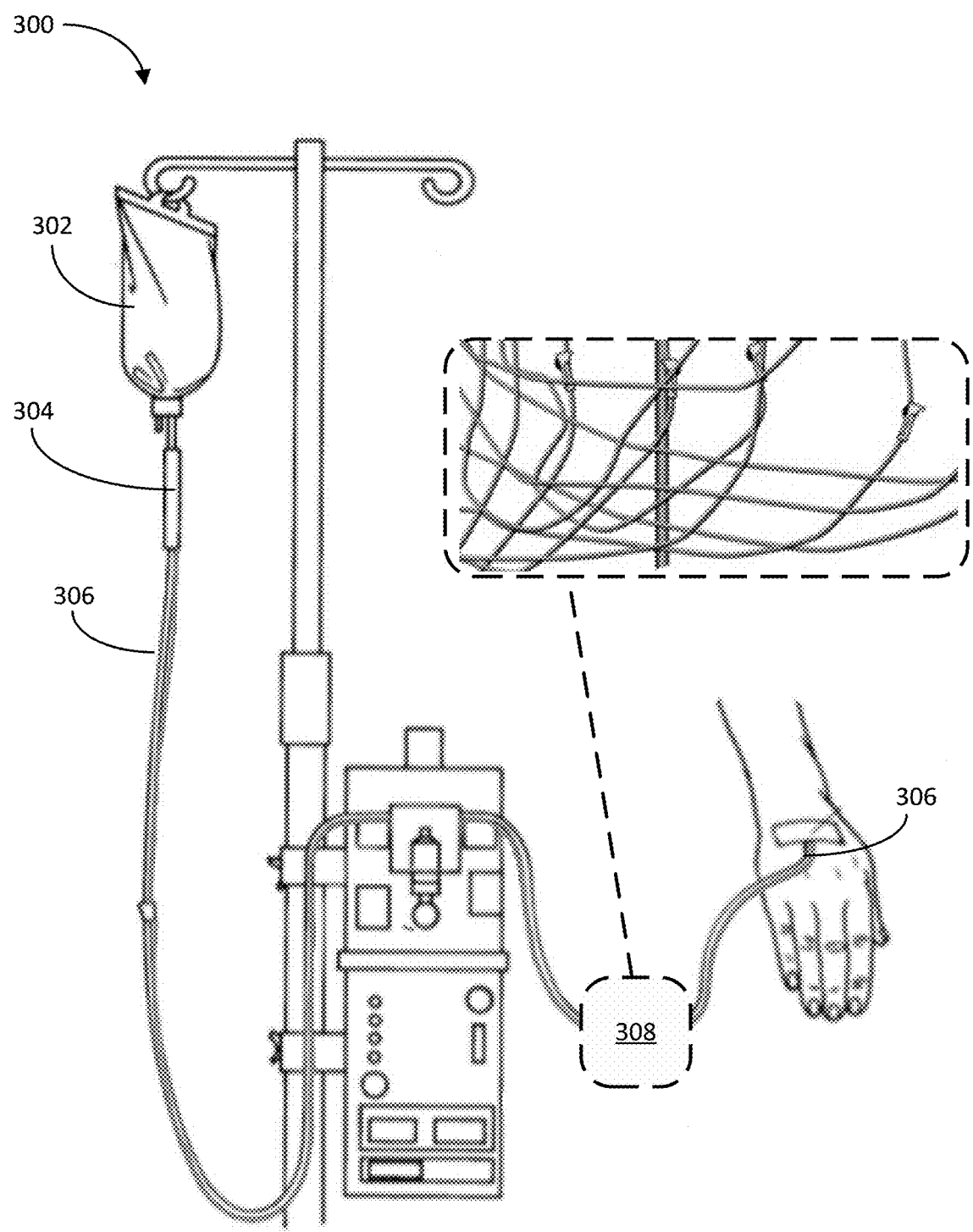
FIG. 3 is a diagram of an IV system including illuminated tubing, in accordance with embodiments of the present disclosure.

Turning now to FIG. 3, an IV system 300 having illuminated tubing 306 is shown, in accordance with embodiments of the present disclosure. The IV system 300 includes an IV bag 302 (e.g., containing a medication) in connection with a drip chamber 304. The contents of the IV bag 302 can be infused via the illuminated tubing 306, which connects to a cannula 306 as inserted into the patient. Notably, the IV system 300 and illuminated tubing 306 may be part of a larger, multi-infusion system (e.g., system 200). Accordingly, the illuminated tubing 306 may be included in a set of tubing 308 exhibiting "spaghetti syndrome." Advantageously, the illuminated tubing 306 may provide a continuous (or substantially continuous) illumination along the IV tubing. As will be described, this results in an extremely efficient line tracing process.

Figure 4A:
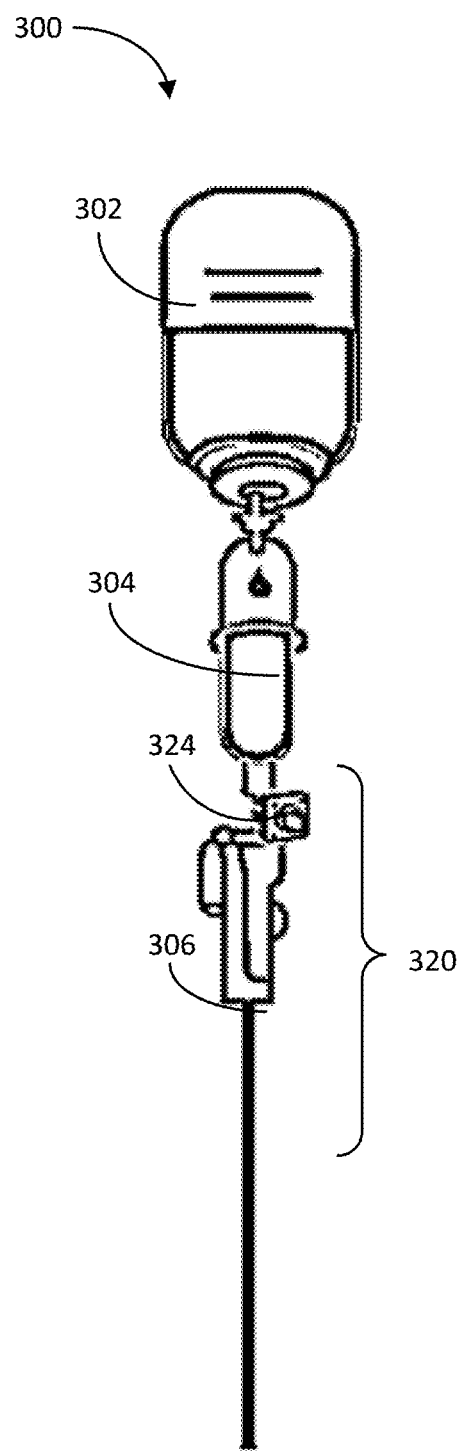
FIG. 4A is a diagram of an IV system including illuminated tubing in an "off" state, in accordance with embodiments of the present disclosure.
Figure 4B:
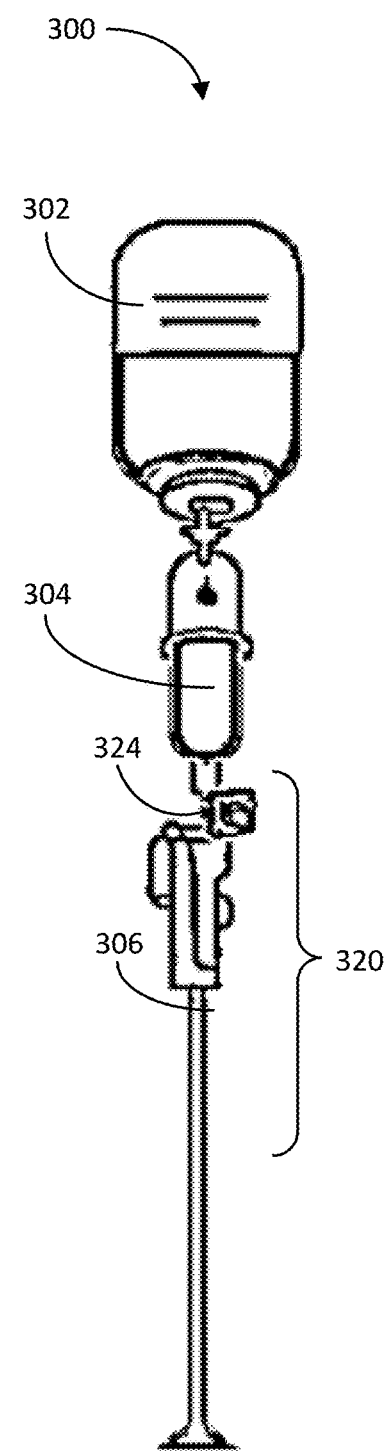
FIG. 4B is a diagram of the IV system of FIG. 4A, including illuminated tubing in an "on" state.

Referring to FIGS. 4A and 4B, the system 300 is shown in additional detail, in accordance with embodiments of the present disclosure. FIG. 4A corresponds to an "off" state of the illuminated tubing 306. Conversely, FIG. 4B corresponds to an "on" state of the illuminated tubing 306. As shown by FIGS. 4A and 4B, an illumination system 320 may be attached below (e.g., adjacent to) the drip chamber 304.

The illumination system 320 can includes the illuminated tubing 306 and a user interface 324. In some configurations, the user interface 324 can include one or more pushbuttons. The pushbutton(s) can be configured to control the lighting of the illuminated tubing 306. As one non-limiting example, a first press of a push button may turn on the light source (FIG. 4B), and a second press of the push button may turn off the light source (FIG. 4A). Additional control configurations are described in the context of FIG. 14, according to embodiments of the present disclosure.

Figure 5:
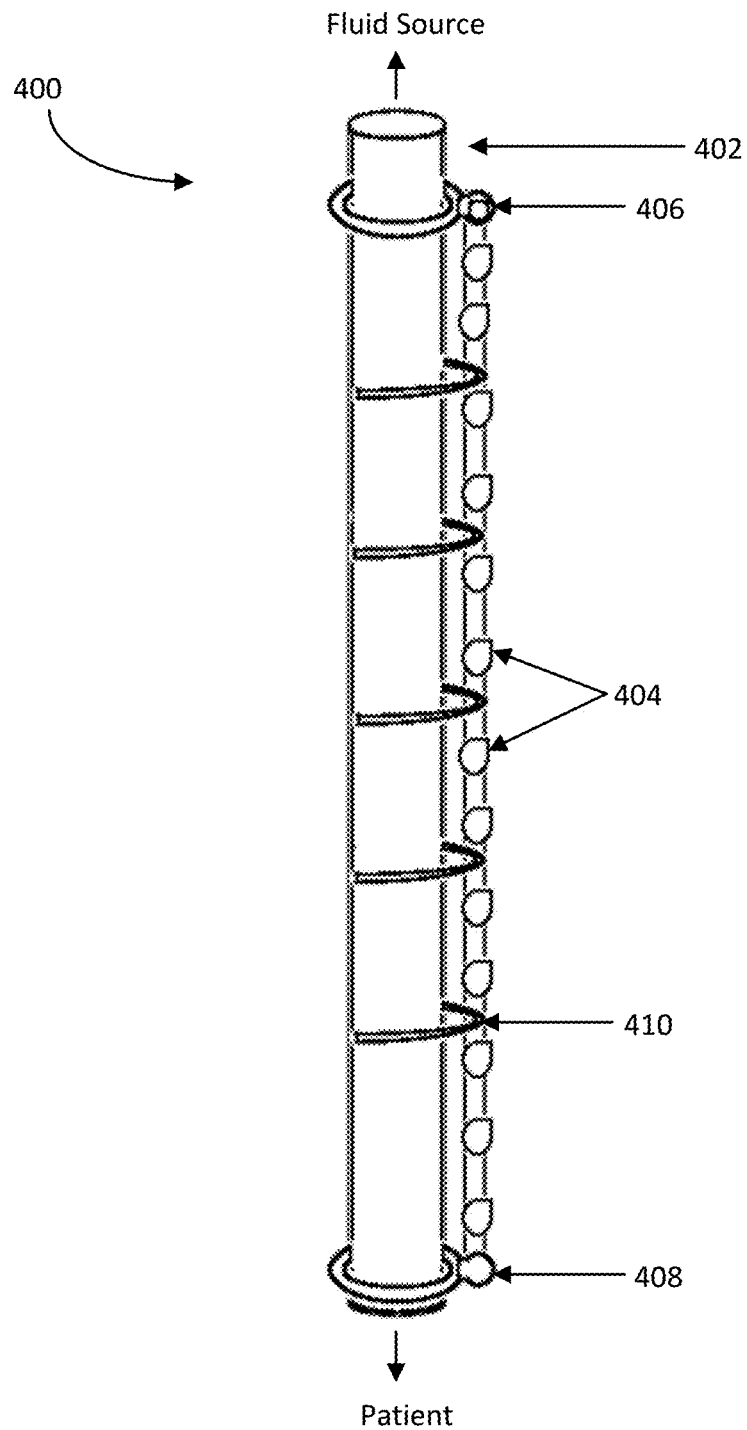
FIG. 5 is a diagram of illuminated tubing, in accordance with embodiments of the present disclosure.
Figure 6:
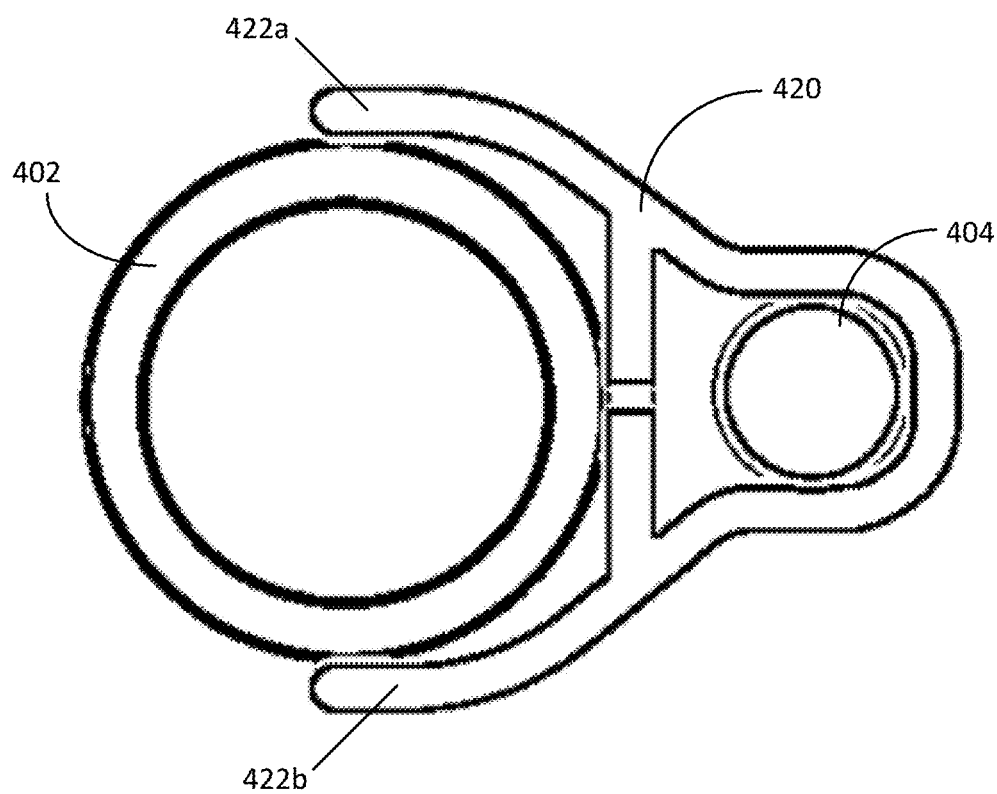
FIG. 6 is a diagram of an illuminated tubing clamp, in accordance with embodiments of the present disclosure.

Referring now to FIGS. 5 and 6, an IV system including illuminated tubing 400 is shown, in accordance with embodiments of the present disclosure. In some configurations, the illuminated tubing 400 can include IV tubing 402 (e.g., standalone tubing, pre-existing tubing), and an illumination strip 404 including a light source. The illumination strip 404 can be configured to provide a continuous length of lighting/illumination. In some configurations, light emitting diodes (LEDs) may be implemented as a light source, and may be distributed along the illumination strip 404. Advantageously, LEDs generate minimal heat, even during prolonged use. Thus, contact between the LEDs and the IV tubing 402 can be safely maintained (e.g., without affecting fluids within the IV tubing 402). Alternatively, electroluminescent (EL) wire can be implemented as a light source, and may be distributed along the illumination strip 404.

In some embodiments, a user interface 406 can be provided proximate to the IV bag. The user interface 406 can include one or more push buttons, and/or a power source. In some configurations, the power source may be a battery. Advantageously, LEDs are very energy efficient, and may last longer (e.g., <100 hours) than other light sources, even when battery-powered.

As shown by FIG. 5, the illumination strip 404 can be configured to removably couple to the IV tubing 402. In some embodiments, a plurality of clamps can be distributed along the illumination strip 404. The clamps can be configured to secure the illumination strip 404 to the IV tubing 402. As such, the illumination strip 404 runs parallel to the IV tubing 402. Although various clamps are described herein, other methods of attaching the illumination strip 404 to the IV tubing 402 (e.g., loops, ties, etc.) are expressly contemplated.

In some embodiments, anchor clamps 408 can be positioned at either end of the illumination strip 404. As shown, for example, an anchor clamp 408 can tightly attach the illumination strip 404 to the IV tubing 402 at the patient. Further, an anchor clamp 408 can tightly attach the illumination strip 404 to the IV tubing 402 at the IV bag (e.g., proximate to a corresponding drip chamber).

Between the anchor clamps, loose c-clamps 410 can be positioned along the illumination strip 404. The loose c-clamps 410 can secure the illumination strip 404 to the IV tubing 402. The "loose" nature of these intermediary c-clamps allows the c-clamps 410 to smoothly slide along the IV tubing 402, which ensures any movement of the patient or the equipment remains unrestricted.

In some embodiments, the illumination strip 404, anchor clamps 408, and loose c-clamps 410 can be provided as a combined "sleeve." By way of example, the combined sleeve can be: 1) placed at one end of the IV tubing 402; 2) secured via an anchor clamp 408; 3) pulled along the length of the IV tubing 402 (providing approximate placements of the loose c-clamps 410); 4) secured via an anchor clamp 408 at a second end of the IV tubing 402; and 5) secured along the IV tubing 402 via the loose c-clamps 410. The combined sleeve can ensure efficient and accurate installation of the illumination strip 404, including on existing (e.g., in-use) medical tubing. Advantageously, installation can occur without disconnecting the patient from the IV bag (i.e., no disruption in treatment occurs). Further, the sleeve can be reused (following cleaning protocols), providing a low cost and efficient system for identifying individual medical tubes/lines.

Referring to FIG. 6, a c-clamp 420 is shown, according to embodiments of the present disclosure. The c-clamp 420 can be the same or substantially similar to the loose c-clamp 410, as shown in FIG. 5. In some configurations, the c-clamp 420 can encircle (fully or partially) the perimeter of the illumination strip 404. The c-clamp can include two arms 422a, 422b configured to engage and retain the medical tubing (e.g., IV tubing 402). In some embodiments, the distance between the two arms 422a, 422b can be selected based on the diameter of the medical tubing. This can ensure a secure fit, without compromising the structural integrity of the medical tubing. In some embodiments, the distance between the two arms 422a, 422b can be approximately 3 millimeters (e.g., within the range of 2.9 to 3.1 millimeters), which corresponds to the diameter of conventional IV tubing.

In some embodiments, the anchor clamps 408 can include an inner ring configured to secure the illumination strip 404, and an outer ring configured to secure the medical tubing (e.g., IV tubing 402). Further, the anchor clamps 408 can include a latch, which allows a user to open and close the clamp (e.g., during installation or adjustment on the medical tubing).

Referring now to FIGS. 7-11, illumination systems 500 and 600 are shown, according to embodiments of the present disclosure. The illumination systems 500, 600 can include medical tubing 502 (e.g., conventional IV tubing), illuminated tubing 504, a light source 506, and an optical junction. Advantageously, the illumination systems 500 and 600 can include modular device components (e.g., illuminated tubing, light source, optical junction), which can be quickly and easily connected (and replaced).

As shown, the illumination system 500 can include an optical junction 508 in the form of a y-junction. In contrast, the illumination system 600 can include an optical junction 608 in the form of a cylinder (e.g., a cylinder with an elliptical cross section). The optical junction 608 can be other shapes and sizes, according to some embodiments. In some configurations, the optical junction 508, 608 may be formed from polycarbonate via injection molding. In some configurations, the optical junction 508, 608 can be secured to an IV bag below the drip chamber, with the medical tubing 502 connecting the drip chamber to the optical junction 508, 608. The illumination input 510 can be connected to the illuminated tubing 504 via the optical junction 508, 608.

Figure 7:
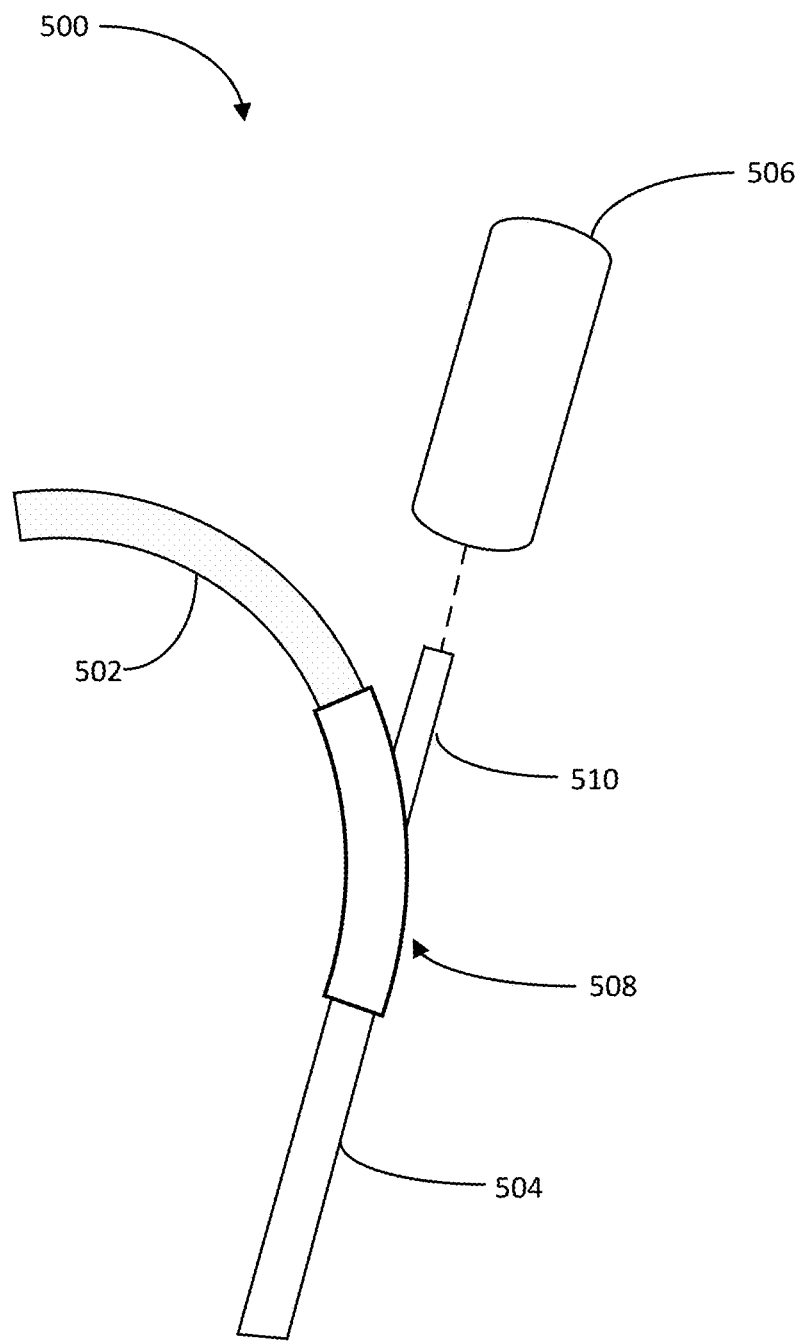
FIG. 7 is a diagram of an optical junction, in accordance with embodiments of the present disclosure.
Figure 9:
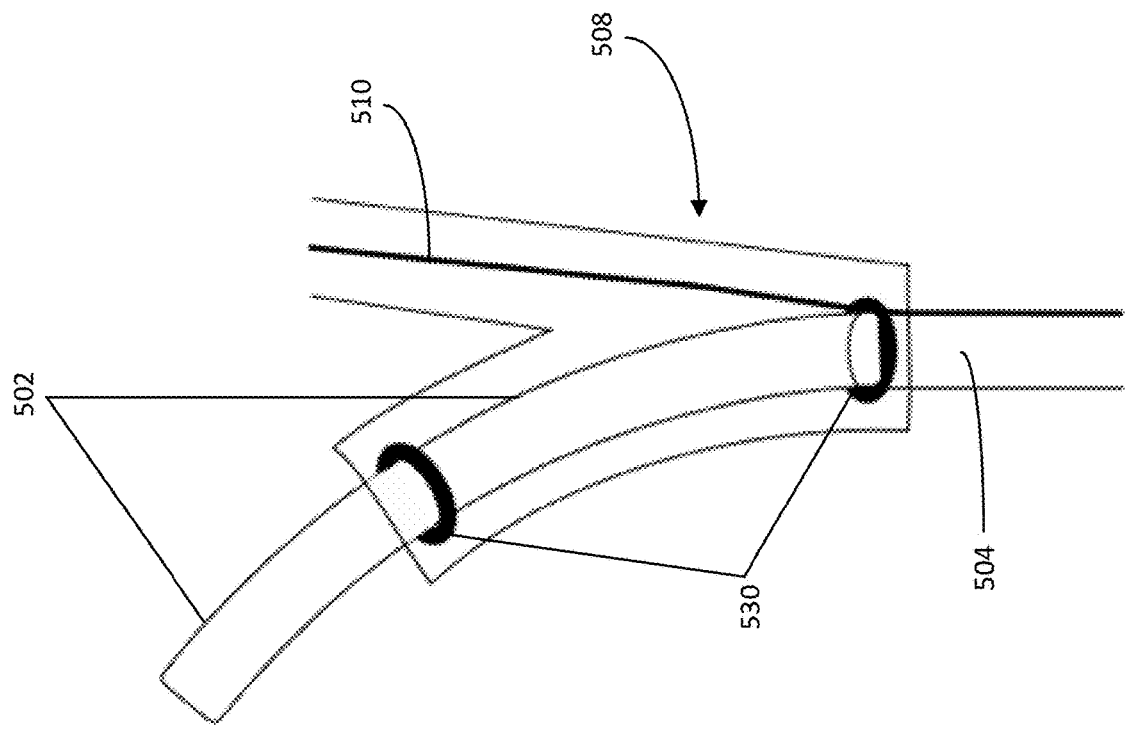
FIG. 9 is a diagram of the interior of another optical junction, in accordance with embodiments of the present disclosure.
Figure 8:
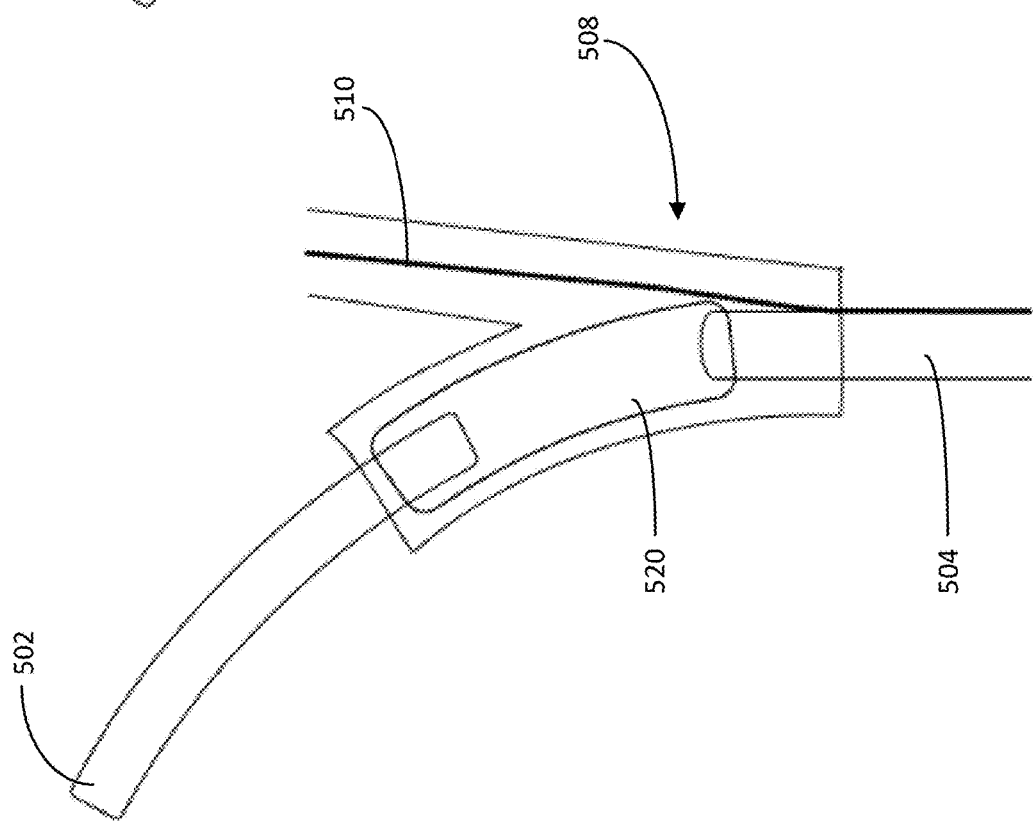
FIG. 8 is a diagram of the interior of an optical junction, in accordance with embodiments of the present disclosure.
Figure 10:
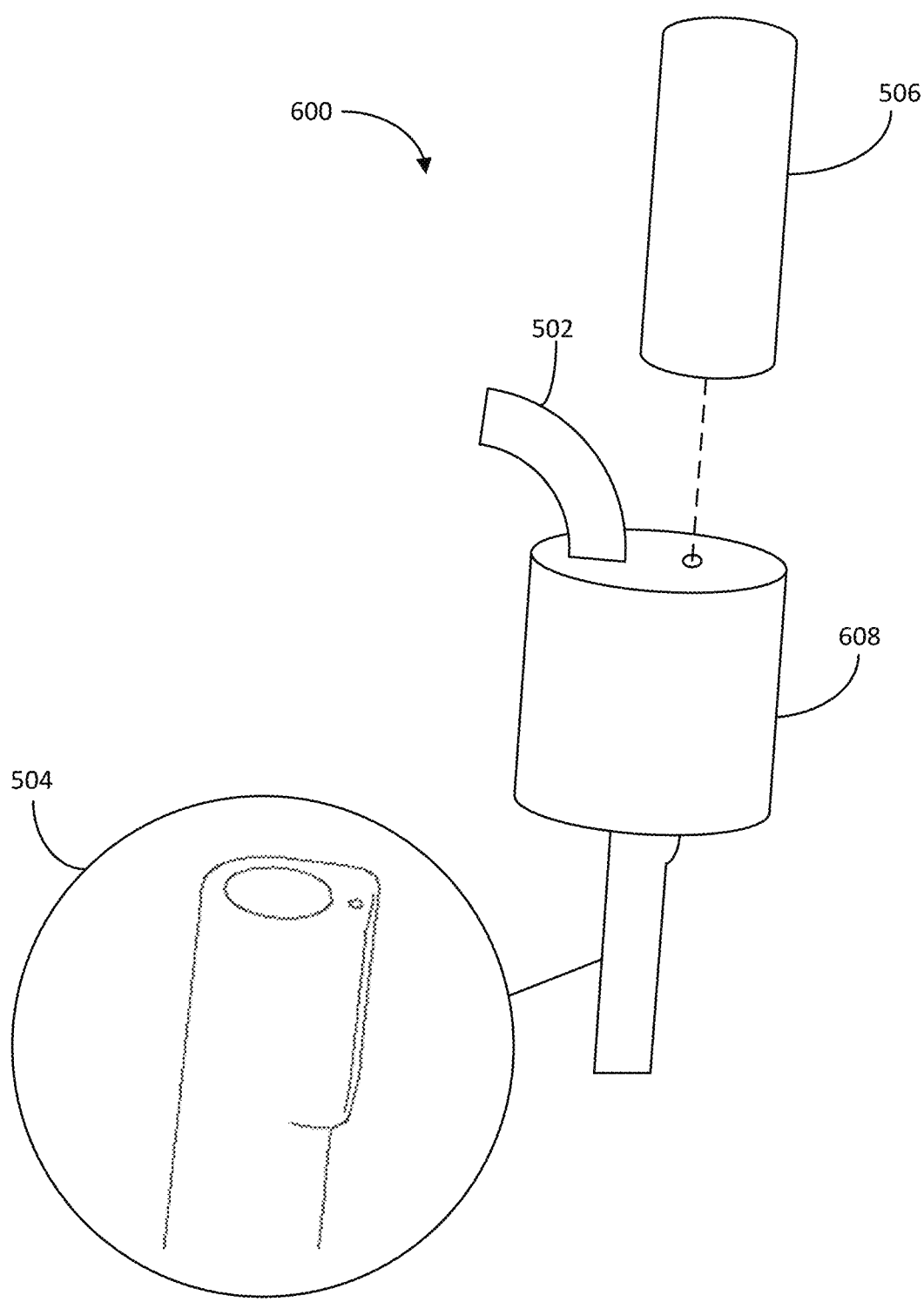
FIG. 10 is a diagram of another optical junction, in accordance with embodiments of the present disclosure.

Referring specifically to FIGS. 7-9, the optical junction 508 can be configured with a first input branch for the medical tubing 502 and a second input branch for the illumination input 510. Further, the optical junction 508 can be configured with an output branch for the illuminated tubing 504. The optical junction 508 may have an exterior formed of hard plastic, or a similar material.

As shown in FIG. 8, the optical junction 508 can include an internal chamber 520, which can couple the medical tubing 502 to the illuminated tubing 504 such that fluid may securely flow from the medical tubing 502 to the illuminated tubing 504. As shown in FIG. 9, the optical junction 508 can include internal junctions 530 (in addition to, or instead of the internal chamber 520). The internal junctions 530 can create a fluid-tight seal for the medical tubing 502 and the illuminated tubing 504. In some configurations, the internal junctions 530 and internal chamber 520 can be formed from a plastic gel, silicone, rubber, polyurethane, and/or neoprene.

Figure 11:
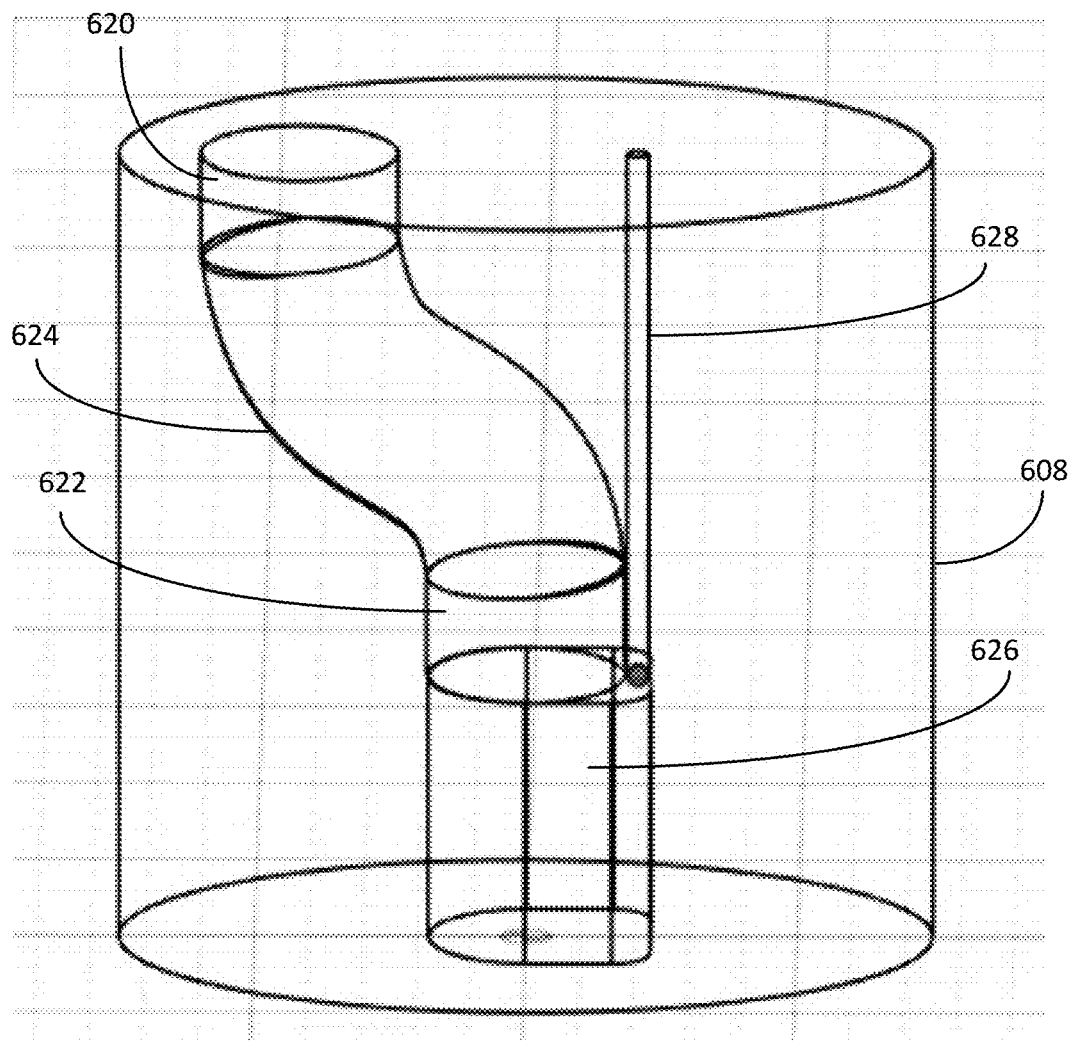
FIG. 11 is a diagram of the interior of the optical junction of FIG. 10.

Referring specifically to FIG. 11, the optical junction 608 is shown to include a medical tubing port 620 and an illuminated tubing port 622. The ports 620, 622 can provide a fluid-tight seal, with a connecting internal chamber 624. The optical junction 608 can further include an internal junction 626 configured to receive and secure the illuminated tubing 504. The illumination input 510 can be connected to the internal junction 626 (and, thus, the illuminated tubing 504) via channel 628, which can be disposed within the optical junction 608.

In some embodiments, the optical junction within the illumination systems 500 and 600 can include or take the form of a luer lock, magnets, Velcro, snap-fit attachment mechanisms, and the like.

In some embodiments (see, e.g., FIG. 10), the illuminated tubing 504 can be a unitary component (i.e., as opposed to an illumination strip attached along a standalone medical tubing). FIGS. 12 and 13 provide examples of unitary illuminated tubing, in accordance with embodiments of the present disclosure.

As shown in FIG. 12, illuminated tubing 700 (which can correspond to illuminated tubing 504) can include a first tube 702 adjacent to a second tube 704. As shown in FIG. 13, illuminated tubing 710 (which can be implemented similarly to illuminated tubing 504) can include a first tube 702 having an interior second tube 704. In some embodiments, the illuminated tubing can be configured with a tear-drop shaped cross-section (e.g., a similar configuration as shown in FIG. 12, with a smoothed exterior). Further, in some embodiments, the illuminated tubing can be configured with an internal tube and a secondary tube spiraled around the internal tube. In this regard, the individual tubes and/or the illuminated tubing may have a symmetrical or asymmetrical cross-section.

In some embodiments, the first tube 702 can be configured to transport fluid, such as fluid from an associated IV bag. The second tube 704 can be configured to house (or transmit light from) a light source (e.g., light source 506). Illuminated tube 710 can, in some configurations, alternatively have the first tube 702 be configured to house (or transmit illumination from) a light source. Thus, the second tube 704 would be configured to transport fluid.

Still referring to FIGS. 12 and 13, as an example, an LED light strip may extend through the second tube 704, and connect to a power source via an optical junction (e.g., optical junction 508, 608). As another example, an EL wire may extend through the second tube 704 and connect to an AC current source via an optical junction. In some embodiments, a glass or optical fiber may extend through the second tube 704, and connect to a light source (e.g., a laser), via an optical junction. In configurations utilizing a laser, a Laser Wire™ cable may extend through the second tube 704. Advantageously, the Laser Wire™ cable does not retain a memory, is significantly flexible, and does not degrade in water or sunlight.

In embodiments configured to transport fluids via the interior tubing, the lighting strip, wire, or fiber may be wrapped around the interior tubing (e.g., in a spiral).

In some embodiments, the laser may be a 20 mW, Class 3R laser, with an input/output voltage of 5V DC. The laser may be any number of colors, including green. In some configurations, the laser can be reusable and secured to an IV pole. In some embodiments, an optical fiber may be used in conjunction with the laser. The optical fiber can have a diameter of about 0.9 millimeters (e.g., within the range of 0.8 to 1.0 mm). The lighted element within the optical fiber may have a diameter less than about 0.2 millimeters (e.g., within the range of 0.1 to 0.2 mm). Advantageously, a laser and optical fiber system can be very cheap. Specifically, the illuminated tubing (including an optical fiber) can be ~$2.30. Thus, the illuminated tubing may be considered disposable. The laser can be ~$6.84, and (as mentioned above) can be reusable between patients, units, etc. (following cleaning protocol). Accordingly, the present disclosure provides a cost effective system.

In some embodiments, each optical junction (e.g., optical junction 508, 608) can be connected to a dedicated light source (e.g., a dedicated laser having a dedicated push button). Alternatively, a light source may include a multi-channel adapter configured to connect with multiple optical junctions. Specifically, a single light source may illuminate multiple lines (together, or individually) via a multi-channel adapter. The multi-channel adapter can be configured to control which line is illuminated by the laser at any given time. In some configurations, the multi-channel adapter may use a single light source to light an individual optical fiber, or multiple optical fibers. The multi-channel adapter may include one or more optical shutters, optical routers, and/or optical switches.

Figure 14:
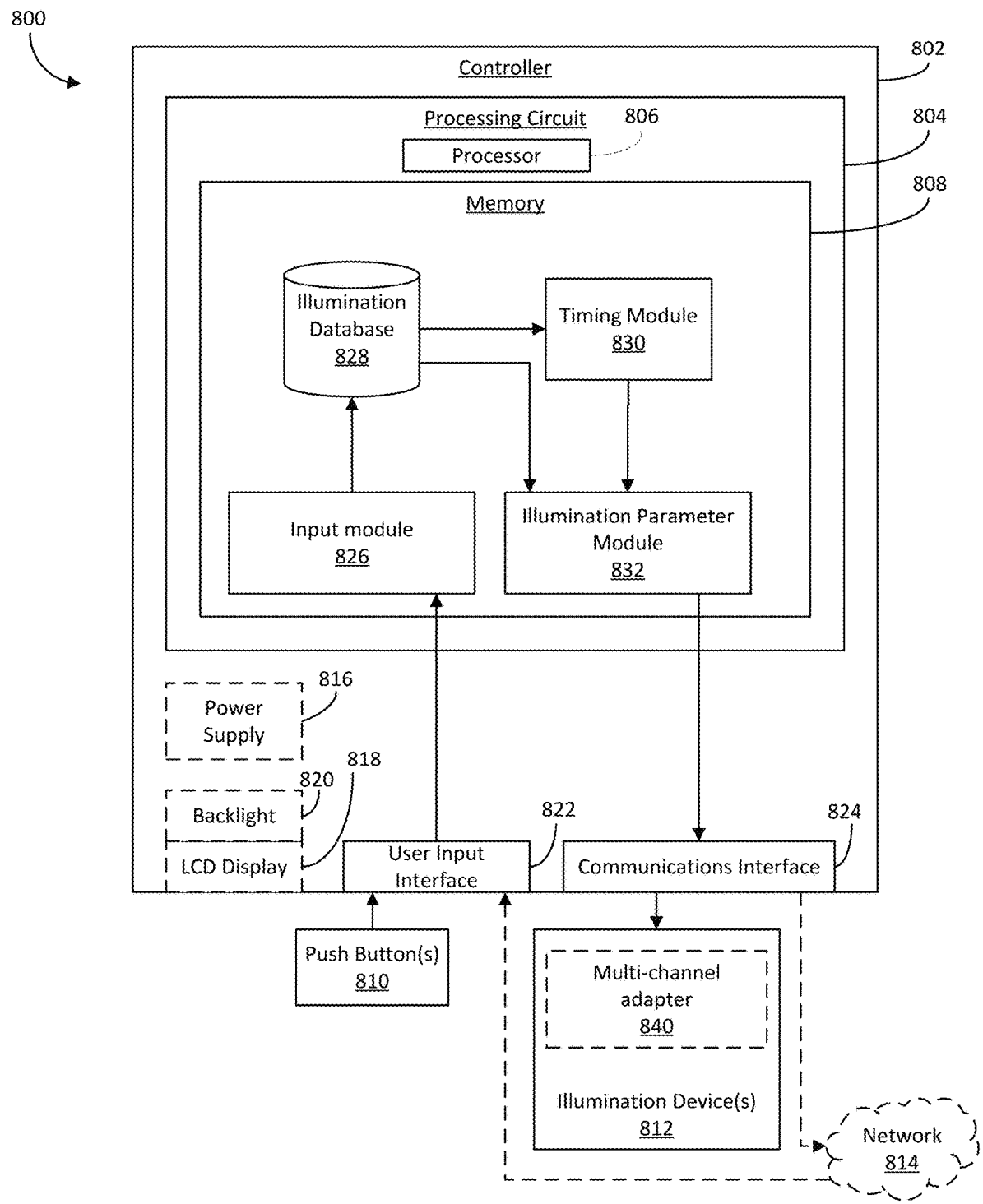
FIG. 14 is a block diagram of an illumination control system, in accordance with embodiments of the present disclosure.

Referring now to FIG. 14, a block diagram of an illumination system 800, including a controller 802, is shown in accordance with embodiments of the present disclosure. The illumination system 800 can be implemented within any of the illumination systems described herein (e.g., systems 300, 400, 500, 600). In some embodiments, the controller 802 can be connected (wired or wirelessly) to push button(s) 810 (or other user interface devices), light source(s) 812, and (optionally) to a network 814.

The controller 802 is shown to include a processing circuit 804, a power supply 816, a communications interface 824, and user interface components (e.g., an optional LCD display 818, an optional backlight 820 for LCD display 818, and a user input interface 822). In various embodiments, power supply 816 can be an optional internal power supply (e.g., batteries). Alternatively, the power supply 816 can provide an interface for receiving power from an external power source. In some configurations, the power supply 816 can optionally provide power to the light source(s) 812 (e.g., illumination strip 404, light source 506).

The LCD display 818 can be an electronic display (e.g., a graphical display, an alpha-numeric display, etc.) configured to present information to a user. The LCD display 818 may be used to display, for example, information about infusion bag contents (e.g., dose, instructions for administration, etc.), and status alerts pertaining to infusion. Backlight 820 can provide backlighting for LCD display 818 and may be illuminated at various levels of brightness.

User input interface 822 can include any of a variety of a user input devices (e.g., push button(s) 810, a keypad, a touch-sensitive display, etc.) for receiving user input. The user input interface 822 can facilitate user interaction with the controller 802, and can allow a user to adjust various parameters stored within the controller 802. In some configurations, the controller 802 may not include a display (e.g., LCD display 818). Additionally or alternatively, data may be wirelessly transmitted from the controller 802 to a network accessible by various servers, display devices, and/or user devices. For example, the controller 802 may be in one-way or two-way communication with a wired or wireless device (e.g., located at a nursing station), the latter being accomplished via one or more cellular and/or radio-type (Bluetooth, WiFi, Zigbee, etc.) transceivers. Such external devices can be configured to display information, and in some embodiments, can accept user inputs that are subsequently transmitted to the controller 802.

The controller 802 can provide a variety of control outputs. Control outputs may be selectively activated or deactivated by processing circuit 804 (e.g., by illumination parameter module 832) to provide a control signal to communications interface 824. Communications interface 824 may include wired or wireless interfaces (e.g., jacks, antennas, transmitters, receivers, transceivers, wire terminals, etc.) for conducting electronic data communications with the light source(s) 812 or other external systems or devices. Such communications can be direct (e.g., local wired or wireless communications) or via a communications network 814 (e.g., a WAN, the Internet, a cellular network, etc.). For example, communications interface 824 can include an Ethernet card and port for sending and receiving data via an Ethernet-based communications link or network.

In another example, communications interface 824 may include one or more radio (e.g., WiFi, Bluetooth, Zigbee, etc.) transceivers or a cellular or mobile phone communications transceiver for communicating via a wireless communications network. Communications interface 824 can be communicably connected to processing circuit 804 such that processing circuit 804 and the various components thereof can send and receive data via communications interface 824.

Processing circuit 804 is shown to include a processor 806 and memory 808. Processor 806 can be implemented as a general purpose processor, an application specific integrated circuit (ASIC), one or more field programmable gate arrays (FPGAs), a group of processing components, or other suitable electronic processing components. Memory 808 (e.g., memory, memory unit, storage device, etc.) can include one or more devices (e.g., RAM, ROM, Flash memory, hard disk storage, etc.) for storing data and/or computer code for completing or facilitating the various processes, layers and modules described herein. Memory 808 can be or include volatile memory or non-volatile memory.

Memory 808 can include database components, object code components, script components, or any other type of information structure for supporting the various activities and information structures described in the present application. According to an exemplary embodiment, memory 808 is communicably connected to processor 806 via processing circuit 804 and includes computer code for executing (e.g., by processing circuit 804 and/or processor 806) one or more processes described herein.

Still referring to FIG. 14, memory 808 is shown to include an input module 826. Input module 826 may receive and store inputs from the push button(s) 810 and the network 814. Input module 826 can store the data with attributes that describe the type of data, the data source, a time at which the data is acquired, and/or other attributes that describe the data. As shown in FIG. 14, the input module 826 may provide the data (e.g., push button status and identification) to illumination database 828.

Memory 808 is further shown to include an illumination database 828, which can communicate with a timing module 830 and the illumination parameter module 832, according to some embodiments of the present disclosure. The illumination database 828 can be configured to store parameters associated with the push button(s) 810 and light source(s) 812. As an example, the illumination database 828 can store information pertaining to which push button corresponds to which infusion line, and which light source corresponds to said infusion line. In some configurations, the illumination database 828 can include information corresponding to a multi-channel adapter 840 (e.g., which channel corresponds to which push button).

Still referring to FIG. 14, memory 808 is shown to include the timing module 830, which can receive data from the illumination database 828, according to some embodiments of the present disclosure. In some embodiments, the timing module 830 can correlate each input (e.g., from the push button(s) 810) to a time it was received. The timing module 830 can additionally store default illumination times corresponding to each push button (and thus, each infusion bag). As an example, in response to a user pressing a push button, the associated light source can turn on for a set period of time. In some configurations, the illumination time can be one minute. Alternatively, the illumination time can be 30 seconds. Such a time enables a user to identify and fully trace the tubing. In some configurations, the illumination time can be predefined by a user during setup and/or use. Additionally, different push buttons can have different illumination times. In some configurations, there may be no set illumination time (i.e., the light source remains "on" until a second user input occurs).

As shown, memory 808 includes an illumination parameter module 832, which can receive data from the illumination database 828 and the timing module 830. The illumination parameter module 832 may store various parameters used in the control of the light source(s) 812. Parameters stored by the illumination parameter module 832 may include, for example, illumination patterns, and brightness values (e.g., as a percentage, power output, etc.). As an example, in response to a user pressing a push button, the associated light source can begin flashing on and off (e.g., at a predefined frequency). As another example, one or more light sources may have a higher brightness value (such as the "emergency medical line"). In some configurations, the brightness value can be updated based on the time of day (as determined by the timing module 830). As an example, it may be advantageous for the light source(s) 812 to have a higher brightness value during the day, when the room is brighter. At night, the brightness value may decrease, when the room is otherwise dark.

According to some embodiments of the present disclosure, the illumination parameter module 832 can provide outputs to the light source(s) 812 and the network 814 via the communications interface 824. Outputs can include, for example, turning on and off a specific light source, turning off a light source after a period of time, and turning on and off a light source based on a set frequency. When the light source(s) 812 include the multi-channel adapter 840, the outputs can be provided to the multi-channel adapter 840 (and may provide information regarding which channel to activate).

Figure 15:
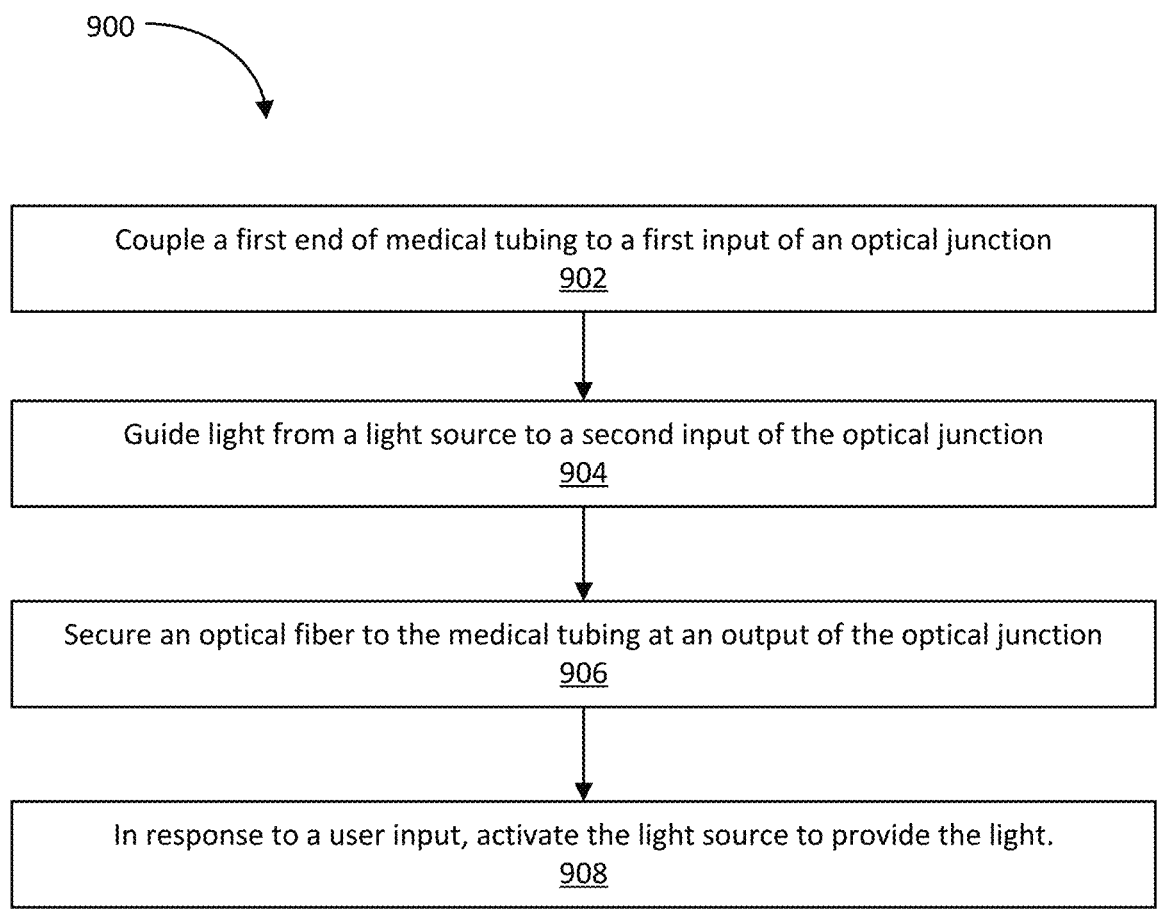
FIG. 15 is a process diagram of a method for illuminating medical tubing, in accordance with embodiments of the present disclosure.

Referring now to FIG. 15, a process 900 for illuminating medical tubing is shown, in accordance with embodiments of the present disclosure. Process 900 is shown to include coupling a first end of medical tubing to a first input of an optical junction (step 902). Process 900 is additionally shown to include guiding light from a light source to a second input of the optical junction (step 904). Process 900 can further include securing an optical fiber to the medical tubing at an output of the optical junction (step 906). Additionally, the process 900 can include, in response to a user input, activating the light source to provide the light (step 908). In some configurations, the process 900 can include additional or fewer steps.

The present disclosure provides systems and methods for illuminating medical tubing. In addition to the benefits already described, a system utilizing illuminated medical tubing (in accordance with the described embodiments) can be a significant asset in isolation units. Decreasing the time spent in close proximity to a patient in isolation decreases the chances of infection transmission. Additionally, in hospitals with limited equipment (or during an outbreak/pandemic), nurses have begun placing IV bags and infusion pumps outside of the patients' room. This enables the doctors and nurses to adjust infusions, while preserving the stock of personal protective equipment (PPE) (which is normally discarded each time a provider exits a patients' room). In accordance with the present disclosure, nurses would be able to activate the light source from outside of the room, while still being able to visually identify the desired medical line (i.e., through a window).

Examples

Over 70 group interviews were conducted with experienced nurses, regarding existing IV identification methods. Stunningly, over 50% of interviewed nurses were unsatisfied with the status quo.

When presented with a continuous lighting system, in accordance with the present disclosure, nurses provided the following feedback:

"long overdue solution"

"this is unbelievable, definitely worthwhile"

"solves a daily problem"

"this would be incredibly helpful keeping lines organized"

"love this, I think all nurses could use this"

"great idea, I'd use it"

Further, time trials were conducted to compare line tracing times for a continuous lighting system (as described herein), and an existing, hand-labeled system. The continuous lighting system reduced the line tracing time by over 50%. Such a significant reduction in tracing time is immensely beneficial in an emergency situation (as is common in the ICU, for example).

Additionally, several nurses were provided with two example systems, in accordance with embodiments of the present disclosure. In particular, "system 1" corresponded to systems 500 and 600, as described above (i.e., a unitary illuminated tubing). "System 2" corresponded to system 300, as described above (i.e., an illumination strip attached to standalone medical tubing).

Regarding system 1, nurses provided the following feedback:

"easy to trace. Subtle device."
"The color is great. Brightness is ideal. Easy to trace"
"I like the continuity of the light."
"easier to see [line/tubing] tangling"

Regarding system 2, nurses provided the following feedback:

"I was able to easily track it."
"nice brightness"

Regarding both systems 1 and 2, nurses provided the following feedback:

"Particularly helpful for the ER setting and for emergency cases. This is a fabulous product."
"not at all" difficult to use either system
"Perfect product!"
"Having an on/off functionality with timer would be great."
Easy to use "when having multiple lines, at night and during [patient] handoffs."
Easy to use for "trauma cases, emergent cases for titratable drugs, ICU setting"
"pediatric patients" would enjoy the "fun color when having several [medical] lines"

Thus, the disclosure provides systems and methods for the illumination of medical tubing. Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A system for illuminating medical tubes, the system comprising:
    an optical fiber secured to and extending along a length of a medical tube;
    a light source configured to transmit a light through the optical fiber;
    a controller in communication with the light source, and configured to control the light source; and
    an optical junction comprising:
        a first input configured to secure a portion of medical tubing;
        a second input configured to receive and direct the light from the light source to the optical fiber; and
        an output configured to secure the optical fiber and the medical tube,
        wherein the first input and the output are fluidly connected via the optical junction, and
    wherein the light illuminates the medical tubing via the optical fiber.

2. The system of claim 1, wherein the optical fiber is secured to the medical tube via co-extrusion.

3. The system of claim 1, wherein the controller is configured to activate the light source in response to a user input.

4. The system of claim 3, wherein the controller is configured to deactivate the light source after a predefined illumination time.

5. The system of claim 3, wherein the controller is configured to pulse the light source at a fixed or variable frequency.

6. The system of claim 1, wherein the optical fiber is secured to the medical tube via a plurality of clamps disposed along the length of the medical tube.

7. The system of claim 6, wherein the plurality of clamps are configured to slide along the medical tube.

8. The system of claim 1, further comprising a multi-channel adapter in communication with the light source and controller, wherein the multi-channel adapter is connected to a plurality of optical junctions.

9. The system of claim 8, wherein the controller is configured to:
    receive a user input;
    determine which channel of the multi-channel adapter is associated with the user input; and
    activate the light source for the determined channel.

10. The system of claim 8, wherein each of the plurality of optical junctions corresponds to one of a plurality of optical fibers.

11. The system of claim 9, wherein the controller is configured to receive the user input from at least one of a push button, a touch-screen, a keyboard, a wired user device, or a wireless user device.

12. The system of claim 1, wherein the illumination of the optical fiber is continuous along the length of the medical tube.

13. A method for illuminating medical tubing, the method comprising:
    coupling a first end of medical tubing to a first input of an optical junction;
    guiding light from a light source to a second input of the optical junction;
    securing an optical fiber to the medical tubing at an output of the optical junction, causing the first input to be fluidly connected to the output of the optical junction and the second input to be connected to the output of the optical junction; and
    in response to a user input, activating the light source to provide the light.

14. The method of claim 13, wherein the optical fiber and the medical tubing are co-extruded or otherwise manufactured as an integrated component.

15. The method of claim 13, further comprising deactivating the light source after a predefined amount of time.

16. The method of claim 15, further comprising pulsing the light source at a fixed frequency for the predefined amount of time.

17. The method of claim 13, further comprising, prior to activating the light source:
    determining a channel corresponding to a multi-channel adapter, based on the user input; and
    providing the light to the optical junction by activating the channel.

18. The method of claim 13, further comprising coupling a second end of the medical tubing to a drip chamber of an IV bag.

19. A system for illuminating medical tubing within a multi-infusion system, the system comprising:

a plurality of illuminating tubes, each illuminating tube comprising a medical tube secured to an optical fiber;
a light source configured to transmit a light through the optical fiber;
a plurality of optical junctions, each optical junction comprising:
  a first input configured to secure a portion of medical tubing;
  a second input configured to receive and direct the light to the optical fiber such that the optical fiber illuminates; and
  an output configured to secure one illuminating tube of the plurality of illuminating tubes,
  wherein the first input and the output are fluidly connected via the optical junction; and
a multi-channel adapter in communication with the light source and each of the plurality of optical junctions,
wherein the multi-channel adapter is configured to selectively provide the light to any one of the plurality of optical junctions.

20. The system of claim 19, wherein the multi-channel adapter selectively provides the light to a desired optical junction in response to a user input.

21. The system of claim 19, wherein the multi-channel adapter is configured to provide the light to only one optical junction at any particular time.

22. The system of claim 19, further comprising a controller in communication with the light source and the multi-channel adapter, the controller configured to:
  receive a user input;
  determine, from the user input, a corresponding optical junction from the plurality of optical junctions;
  retrieve, from a controller memory, information associated with an infusion bag, wherein the infusion bag is fluidly connected to the first input of the corresponding optical junction; and
  output the information associated with the infusion bag to at least one of a user device or a display.

23. The system of claim 19, wherein the light source is a laser or at least one light-emitting diode.

* * * * *

EX PARTE REEXAMINATION CERTIFICATE (12552nd)

United States Patent
Lebhar et al.

(10) Number: US 11,221,440 C1
(45) Certificate Issued: Mar. 22, 2024

(54) SYSTEMS AND METHODS FOR ILLUMINATION OF MEDICAL TUBING

(71) Applicant: DUKE UNIVERSITY, Durham, NC (US)

(72) Inventors: Michael Lebhar, Durham, NC (US); Konstantinos Economopoulos, Durham, NC (US); Anshu Jonnalagadda, Durham, NC (US); Shikha Sharma, Durham, NC (US); Kevin Tian, Durham, NC (US); Jacqueline Vaughn, Durham, NC (US); Paul Fearis, Durham, NC (US); Eric Richardson, Durham, NC (US)

(73) Assignee: DUKE UNIVESITY, Durham, NC (US)

Reexamination Request:
No. 90/019,148, Feb. 2, 2023

Reexamination Certificate for:
Patent No.: 11,221,440
Issued: Jan. 11, 2022
Appl. No.: 17/225,679
Filed: Apr. 8, 2021

Related U.S. Application Data

(60) Provisional application No. 63/007,007, filed on Apr. 8, 2020.

(51) Int. Cl.
*F21V 8/00* (2006.01)
*A61M 39/08* (2006.01)
*F21V 21/088* (2006.01)
*F21V 23/00* (2015.01)
*F21V 23/04* (2006.01)
*F21Y 115/10* (2016.01)

(52) U.S. Cl.
CPC ............ *G02B 6/001* (2013.01); *A61M 39/08* (2013.01); *F21V 21/088* (2013.01); *F21V 23/003* (2013.01); *F21V 23/04* (2013.01); *G02B 6/0006* (2013.01); *A61M 2205/587* (2013.01); *F21Y 2115/10* (2016.08)

(58) Field of Classification Search
None
See application file for complete search history.

(56) References Cited

To view the complete listing of prior art documents cited during the proceeding for Reexamination Control Number 90/019,148, please refer to the USPTO's Patent Electronic System.

*Primary Examiner* — Henry N Tran

(57) ABSTRACT

A system for illuminating medical tubes is disclosed. The system includes an optical fiber secured to and extending along a length of a medical tube, and a light source configured to transmit a light through the optical fiber. The system further includes a controller in communication with the light source, and configured to control the light source. Additionally, the system includes an optical junction having a first input configured to secure a portion of medical tubing, a second input configured to receive and direct the light from the light source to the optical fiber, and an output configured to secure the optical fiber and the medical tube. The first input and the output are fluidly connected via the optical junction. The light illuminates the medical tubing via the optical fiber.

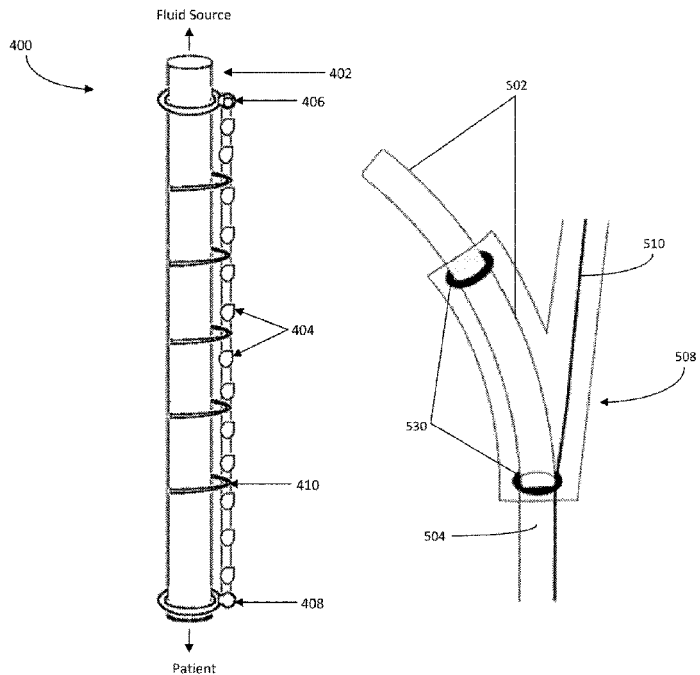

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 19-23 is confirmed.

Claims 1 and 13 are determined to be patentable as amended.

Claims 2-12 and 14-18, dependent on an amended claim, are determined to be patentable.

1. A system for illuminating medical tubes, the system comprising:
- *an illuminating tube comprising* an optical fiber secured to and extending along a length of a medical tube;
- a light source configured to transmit a light through the optical fiber;
- a controller in communication with the light source, and configured to control the light source; and
- an optical junction comprising:
  - a first input configured to secure a portion of medical tubing;
  - a second input configured to receive and direct the light from the light source to the optical fiber; and
  - an output configured to secure [the optical fiber and the medical tube] *the illuminating tube*, wherein the first input and the output are fluidly connected via the optical junction, and
- wherein the light illuminates the medical [tubing] *tube of the illuminating tube* via the optical fiber *when the illuminating tube is received by the output of the optical junction*.

13. A method for illuminating medical tubing, the method comprising:
- coupling a first end of medical tubing to a first input of an optical junction;
- guiding light from a light source to a second input of the optical junction;
- securing an *illuminating tube comprising an* optical fiber *coupled* to [the] *a length of a* medical [tubing] *tube* at an output of the optical junction, causing the first input to be fluidly connected to the output of the optical junction and the second input to be connected to the output of the optical junction *such that light received by the second input from the light source is directed onto the optical fiber of the illuminating tube*; and
- in response to a user input, activating the light source to provide the light.

\* \* \* \* \*